US 6,659,338 B1

(12) United States Patent
Dittmann et al.

(10) Patent No.: US 6,659,338 B1
(45) Date of Patent: Dec. 9, 2003

(54) METHOD AND DEVICE FOR WITHDRAWING BIOLOGICAL SAMPLES

(75) Inventors: Thomas Claus Dittmann, Berlin (DE); Ivo Glynne Gut, Berlin (DE); Arno Svend Heuermann, Berlin (DE); Alexander Olek, Berlin (DE)

(73) Assignee: Biopsytec GmbH, Berlin (DE)

( * ) Notice: Subject to any disclaimer, the term of this patent is extended or adjusted under 35 U.S.C. 154(b) by 0 days.

(21) Appl. No.: 09/508,144

(22) PCT Filed: Sep. 11, 1998

(86) PCT No.: PCT/DE98/02759

§ 371 (c)(1),
(2), (4) Date: Mar. 7, 2000

(87) PCT Pub. No.: WO99/12475

PCT Pub. Date: Mar. 18, 1999

(30) Foreign Application Priority Data

Sep. 11, 1997 (DE) .......................................... 197 40 429

(51) Int. Cl.$^7$ ................................................. G06F 17/00
(52) U.S. Cl. .................. 235/375; 235/385; 235/462.01; 235/462.15; 235/449
(58) Field of Search ................................ 235/375, 385, 235/462; 422/65, 102; 600/566, 573

(56) References Cited

U.S. PATENT DOCUMENTS

| | | | | | |
|---|---|---|---|---|---|
| 4,678,894 | A | * | 7/1987 | Shafer | 235/375 |
| 4,857,716 | A | * | 8/1989 | Gombrich et al. | 235/462 |
| 5,164,575 | A | * | 11/1992 | Neeley et al. | 235/472 |
| 5,281,394 | A | * | 1/1994 | Holub | 422/65 |
| 5,451,374 | A | * | 9/1995 | Molina | 422/99 |
| 5,575,293 | A | * | 11/1996 | Miller et al. | 128/752 |
| 5,591,974 | A | * | 1/1997 | Troyer et al. | 250/336.1 |
| 5,725,261 | A | * | 3/1998 | Rahm | 292/307 |
| 5,777,303 | A | * | 7/1998 | Berney | 235/375 |
| 5,810,806 | A | * | 9/1998 | Ritchart et al. | 605/46 |
| 5,897,989 | A | * | 4/1999 | Beecham | 435/5 |
| 5,965,090 | A | * | 10/1999 | Fanning et al. | 422/65 |

* cited by examiner

*Primary Examiner*—Michael G. Lee
*Assistant Examiner*—Ahshik Kim
(74) *Attorney, Agent, or Firm*—Kreigsman & Kreigsman

(57) ABSTRACT

The invention relates to a method and device for withdrawing biological samples. The device has a receptacle which can receive one or several covers for sample containers, another receptacle which can receive one or several sample containers, and a mechanism. Said mechanism joins the covers and containers together during a working cycle in which the biological sample is withdrawn either through the cover or the sample container to a test capsule.

39 Claims, 13 Drawing Sheets

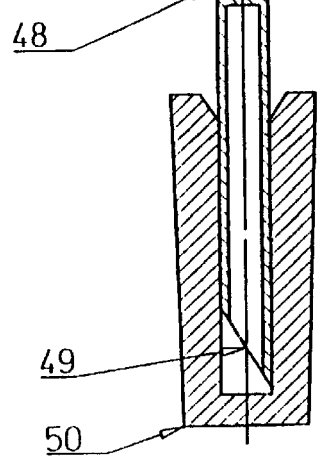
FIG 9
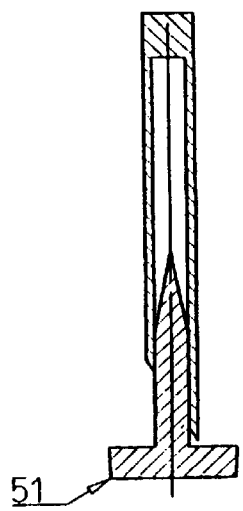
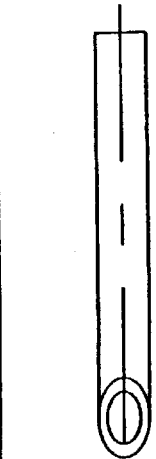
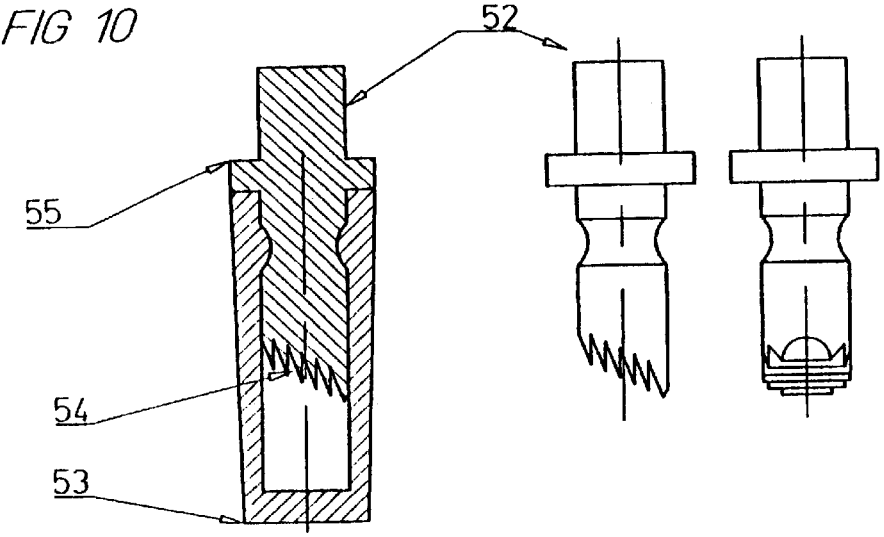
FIG 10
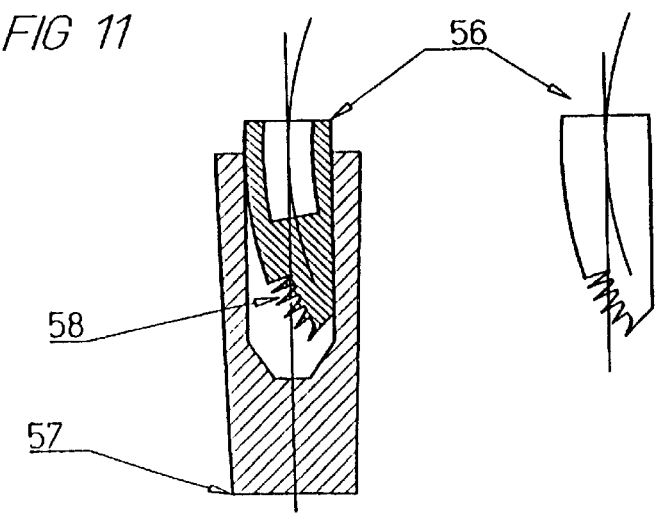
FIG 11

METHOD AND DEVICE FOR WITHDRAWING BIOLOGICAL SAMPLES

DESCRIPTION

1. Field of the Invention

Very different requirements are made with respect to the withdrawal and handling of biological specimens. These relate to quantity, purity, reliability and in several cases, in fact, the speed at which they are taken. New, rapid analytical methods make necessary the simplification of sampling, in order to achieve a decrease in the total analysis cost. High requirements are placed also on the logistics of such a process, due to the withdrawal of large numbers of samples Large numbers of biological analyses are of importance in medicine, research, breeding [cultivation], quality-control and environmental technology. In all these fields, the following parameters determine the requirements that are placed on a sampling system.

1) The number of samples to be taken.
2) The degree of centralizing of the analyses, i.e., whether samples taken at several points in large quantity are processed at one site, where the sorting process for the analytical process must occur efficiently. Another requirement, the labeling of samples, is derived from such a situation, as [also] in the case of a decentralized analysis of the same number of samples.
3) The quantity of data to be processed for the analysis.
4) The degree of training of the personnel who withdraw the samples.
5) The price that an analysis costs and the price that the analysis should cost, measured according to the value of the organism to be investigated.
6) The tolerance of the sampling and the analytical system to errors.
7) The time required for the individual samples to be removed.
8) The quantity and uniformity of the sample volume which must be withdrawn or filled per sampling.

Depending on the application, several of the above-named items have greater or lesser importance. The invention concerns a method that serves to overcome the logistics problems in sampling, recording and processing huge quantities of samples.

Ersatzblatt (Regel 26)=Substitution page (Regulation 26)—written at the bottom of each page—Translator's note.

2. Prior Art and Objectives in Human Medicine

The prior art in the withdrawing of medical samples varies greatly, depending on the application. In principle, biopsies can be differentiated from simple blood, urine or saliva samples.

Various designs of biopsy needles, even automated designs (Burbank et al. U.S. Pat. No. 5,526,822) are known, but all of these are constructed for the withdrawal of small specimens under difficult surgical conditions. These devices require a considerable degree of training. In addition, these devices must be sterilized after use and the samples must be individually packed and labeled.

Consequently, all biopsy devices according to the prior art are constructed for applications other than the method according to the invention and do not fulfill the requirements that are placed on it.

In the withdrawing of saliva, mucus or pus, there are also variants in which the actual sample remover, which is often, e.g., absorbent cotton or folded fabric, is attached directly in the cover of the future specimen container (Holzhäuser et al. DE 3,247,719 A1). The specimen is taken, the cover with the empty container is screwed on or otherwise engaged, so that the cotton wad or folded fabric comes to lie inside the container. These containers are usually provided with a self-adhering barcode.

3. Prior Art in Cattle Breeding

In the case of cattle breeding, for genetic engineering investigation, which has been conducted as yet only to a small extent, the tissue sample is removed by introducing several hair roots of the animal into a sample container. The sample container is sealed and manually inscribed with a numerical code or concrete data. This method does not represent a satisfactory solution, since in the case of large livestock, much time is required due to the many operating steps. It is shown in practice that if the person who withdraws the samples is not directly familiar with specimen analysis or has not been specially trained, irregularities may occur with respect to the quantity of the sample, impurities of the sample or even test capsules without content or with falsified content. Milk cows and the cattle raised for meat production are subject to very different regulations, which prescribe repeated standard investigations. In these cases, among other things, blood samples are withdrawn by a veterinarian. Several special investigations presently do not require blood samples and could theoretically be replaced without problem by a very small tissue sample. Animal breeders and fatteners could save considerable veterinary costs by a method for withdrawing tissue that is simple to manipulate.

Throughout Europe, the registration of cattle has been undertaken starting from Jan. 1, 1998, so that each calf is provided with two ear marks within the first month of life—one in each ear. The country of origin (e.g., DE for Germany, GB for England, etc.) of the animal and a registration number composed of several digits is recorded on both marks. In many cases also, a barcode is used in addition to the number. The only security from loss and misuse is that an animal bears two ear marks with an identical data set. Based on the size of the ear marks, these are very frequently torn off, so that only one mark remains on the animal. A new mark with a corresponding code must be requested from the cattle raising association. In the case of spotted cattle, a drawing replaces the labeling of the respective animal. This drawing is later replaced by a Polaroid picture of the calf. However, since Brown cattle are primarily used for meat production, this additional control is omitted in essential cases. Numbers of ear marks and markings are established in the handbook of the association of the respective country. Tests have also been conducted with subcutaneously implanted transponders. However, these devices can migrate into the body of the animal over the course of its life, so that they can no longer be found during slaughtering and can end up in sausage.

4. Prior art in Plant Cultivation

The diagnosis of infectious diseases in agriculturally important plants would be evaluated as a primary application.

Presently there is no system, which is able to efficiently conduct the withdrawing and clear labeling of the millions of samples and their centralized processing. At the present time, all samples are taken manually, at most with the help of "forceps" and placed in a labeled vessel with tweezers or by hand. The quantities of the removed tissue are not constant, so that each step of the further processing of the samples requires manual intervention, which can lead to errors. Since a presymptomatic procedure often seems troublesome, there is the danger that deliberately false samples will be taken, if the result is not directly utilized. A farmer in fact could fear loss due to the ordered destruction of an entire harvest. In this way, circumstances are provided for intentional fraud. Nevertheless, if a presymptomatic system is to be introduced, certain controls are necessary. The cheaper such a method is, then the greater the need for conducting such controls by automated techniques.

Huge quantities of samplings are necessary for cultivation efforts. In the case of cultivation, the plants must be characterized and one must be able to accurately trace the sample back to its origin, but these methods require an enormous organizational expenditure. Since these methods are still usually conducted manually at the present time, cultivation efforts require considerable expenditure of personnel. This is the primary cost factor in the cultivation of new varieties.

The development of genetically manipulated plants is an enormous investment for the grower. Of course, every grower wants the results of his efforts to be secured legally against unpermitted copying. In theory, the legal basis is given for this. Nevertheless, reliable protection is based on controls. The trade of seed material is global. It is conceivable that huge quantities of random samplings [spot checks] must be performed worldwide in order to conduct these controls. Each individual sample in such a system, nevertheless, must be clearly assigned to its respective source.

Another problem, which has been caused by modern biotechnology, is the control or monitoring of seeds and agricultural products for genetic manipulations. In many cases, consumers desire such controls and at the present time, the regulatory mechanisms are created for such controls. On the technical side, such a control also requires, in addition to the extremely rapid and inexpensive analysis, a high degree of logistics relative to withdrawing samples and recording.

Along with the developments in the field of DNA analysis itself, the widespread and cost-favorable application of these highly promising techniques requires an improved methodology, logistics, equipment and very generally, a much higher degree of automation. The method according to the invention comprises devices and a detailed design for logistics and data transmission and management, which can overcome these problems. The rapid development in the analysis of biological samples will only be used profitably with the necessary logistics support.

A few methods and devices exist in the field of this invention. In fact, e.g., cattle are registered, but there is no simultaneous removal of a tissue sample, in order to prepare a genetic fingerprint therefrom, whereby the false security of registration could be very much overestimated. A device has been described, with which biopsies can be taken serially in humans. What makes the invention described here meaningful are new developments in the analysis of biological samples. An individual analysis with very great sensitivity can be conducted in less than one second by means of DNA mass spectrometry. In this way, requirements that do not as yet exist will be placed on the performance of withdrawing samples and on the management of the samples taken. A method and device for withdrawing biological tissue samples can be utilized with slight modifications for withdrawal of tissue of humans or of plants. The proposed method comprises devices that can solve these problems in a way that has not previously existed.

The current prior art of the analysis of biological samples permits a continuously more efficient processing of extremely large sample quantities. Modern medical diagnosis, forensic medicine, genetically supported plant cultivation, quality controls of biological material and preparation of genetic geneology of humans and animals are conducted to an increasing degree with huge numbers of samples. Thus extremely high requirements are placed on taking samples and sample management. In particular, the development of increasingly more costfavorable DNA analysis opens up applications, which were previously not of interest economically for reasons of cost. In this way, DNA technology can expand to agricultural applications. This involves the removal and data processing of millions of biological samples. New standards for avoiding mixing these up and preventing intentional misuse must be established. Modern DNA technologies are very sensitive, so that impurities must be excluded. Due to disorders that are transmitted to humans by diet, new requirements are produced for withdrawal of samples in order to monitor their origin. At the present time, this monitoring is often bypassed for economical reasons. There is no method and there is no device, which can fulfill the requirements that these new applications of analysis of biological samples require. According to the prior art, the withdrawal of millions of biological samples is uneconomical. Still fewer of the devices available today can remove such quantities of samples with the avoidance of contamination. The withdrawal of large numbers of samples at the present time cannot be conducted with the exclusion of mixing up samples due to human error. In addition, the prior art permits the recording and processing of all data relevant to huge numbers of samples and their processing only with considerable personnel expenditure. In addition, all existing systems of sample withdrawal are based on the willingness of the personnel to conduct these correctly and to be ready to provide correct information for each sample. It is the . . .

A sentence begins at the bottom of page 5 but is not completed on page 6-Translator's note.

As has been described in the prior art, cattle have been characterized with two ear marks throughout Europe, starting from Jun. 1, 1998. Ear marks can be falsified and it cannot be established by means of these marks, whether the finally purchased meat product also originates from the animal that is indicated in the accompanying papers. A complete control of the origin of meat has been required since the occurrence of bovine spongiform encephalopathy (BSE, mad cow disease). Unfortunately it is a fact that almost any member of the meat chain (viewed from the individual handler to the consumer) can, under certain conditions, have an interest in bypassing the existing control or monitoring mechanisms.

OBJECT OF THE INVENTION

The object of the invention is to eliminate the disadvantages that have become clear in the description of the prior art. A device and a method will be made available, which make possible a withdrawal of biological samples in large numbers of units, while simultaneously extensively excluding a falsification due to intentional misuse or mixing up the samples by human error, by means of extensively automating the sample withdrawal itself, as well as coupling the recording of the sample data directly by means of the device. The object of the invention is to make available for the first time a method and the devices for carrying it out, which make possible the development of logistics for processing huge numbers of samples.

SOLUTION TO THE TECHNICAL PROBLEM ESTABLISHED

The method according to the invention makes possible the solution of the object in that:

a sample withdrawal device with components of a test capsule is loaded;

one loaded part of the test capsule removes a tissue sample;

the sample-withdrawal part of the test capsule is joined, by means of the withdrawal or during or after the actual withdrawal, with at least one other part of the test capsule to make up a rigidly sealed unit, the test capsule;

in which subsequent processing steps can be conducted;

the device used for the sample removal can either read the labeling of sample containers automatically or this information can be received from the user and processed;

data on the identity of the sample to be withdrawn are automatically or manually entered;

the data on the serial numbers of the sample vessels are automatically associated with the data on the samples by the withdrawal device;

data on sample vessel number and sample are filed on a common storage medium;

the stored data are transmitted to the analytical device by means of direct data transmission from the withdrawal device or an additional device from or through transport of a separable data carrier.

Within the method, withdrawals of tissue samples are conducted by punching, shooting, scraping, pinching, knocking against [guided shooting] or by tearing out hairs with a part or parts of a test capsule. In one form of embodiment, the user must enter or confirm data in the device designed for the method before each sample withdrawal or before a series of sample withdrawals, in order to trigger the device. This, together with other essential steps of the method, leads to the fact that all operating steps necessary for withdrawing samples and labeling are coupled together in such a way that none of the operating steps can be conducted individually. Thus several components of the method lead to a high security against errors or deliberate false conducting of the method. A labeling of the organism from which a sample is removed can be conducted during or coupled to the actual sample removal. In addition, the labeling cannot be removed after it is introduced on the organism, or it can be removed only by damaging or disrupting the organism. As a carrier, one of the following can be used:

a barcode, a readable and/or writable integrated circuit, a magnetic strip, a transponder, a transmitter, a numerical code, a letter code, or a comparable coding or information carrier system or a simple color labeling, a circumstance which [permits] a logical and completely documentable association between the sample that is removed and the animal from which the sample has been taken, an association that can be broken apart only with great difficulty. Therefore the labeling can no longer be separated without damaging the labeling or the animal and the samples can no longer be manipulated without damaging the test capsule. Thus, the high requirements for the problems of sample withdrawal, recording and security from falsification, as well as their logistics, which have not been solved by the prior art, are now solved.

For conducting the method, a device is particularly produced, which makes available a receptacle, which can receive one or more covers for the sample container (test capsule cover), and also makes available a receptacle, which can receive one or more sample containers, and makes available a mechanism, which joins the test capsule cover and the sample container in one working cycle in which the biological sample is removed either by the test capsule cover or by the sample container, to make up the test capsule.

The particular efficiency of the withdrawal process performed by the device is accomplished by the use of automatic and semiautomatic processes during use, which are essentially characterized by the fact that these make available a mechanism, which, after placement of the device on the tissue and actuating the trigger mechanism, punches or "shoots" a component of a test capsule, as a type of striking pin, through the tissue, in such a way that a tissue sample is withdrawn and the sample remover is joined in the same course of motion with another part of the test capsule to form the closed test capsule. This avoids any manual sealing, and consequently comprises a complete working cycle. Further, the time spent in loading the device is minimized by the fact that it contains one or more magazines, in which individual test capsule covers, sample containers and parts of labelings can be loaded and also makes available a mechanism, which shifts these components of a test capsule by one position in the direction of a sample withdrawing mechanism of the device, by actuating a trigger mechanism jointly within the magazine. In addition, the test capsule covers from a magazine are placed automatically by a mechanism onto the axis of the firing pin and the sample containers of a magazine are placed on the target side of the device. The great variability of the device for the most varied applications within the different possible applications is accomplished by the fact that the device makes available a mechanism, which, in a first step, presses together the sample-withdrawing part of the test capsule when the device is placed on the tissue, and after actuating the trigger mechanism, a tissue sample is removed by a pinching motion; or, in a first step, advances the sample-removing part of the test capsule to the tissue when the device is placed on the tissue, and after actuating the trigger mechanism, such that a tissue sample is removed by a scraping motion, or in a first step advances the sample-removing part of the test capsule to the tissue when the device is placed on the tissue, and after actuating the trigger mechanism, while squeezing the sample remover together, hairs are torn out; and then in another step of the same course of movement or a repeated actuation of the trigger mechanism the sample remover is joined with another part of the test capsule to form the test capsule. Since the most varied types and thus the most varied strengths and thicknesses of tissues must be subjected to a sample removal, the part of the device bearing the sample container and the part bearing the test capsule cover of the device can be pressed rigidly onto the tissue from opposite sides, so that a mechanism found on one of the two sides can use a part of the test capsule for sample removal, and the thus-exercised pressure and the distance between the part of the device bearing the sample container and the part of the device bearing the test capsule cover can be regulated by an adjusting screw or an analogous device.

The enormous logistics problems, which arise in the withdrawal, recording, labeling, shipping and processing of huge quantities of samples, are resolved by a number of novel features according to the invention. First, recording is decisively simplified by the fact that the device makes available a possibility for data entry and/or for data output or is coupled to such a unit. This can be a numerical or alphanumerical keyboard and/or a device for receiving or for reading of data. Therefore, the device is characterized by the fact that it makes available a mechanism or electronic unit, by means of which data such as the serial number of the sample container or several sample containers linked together and/or information on the organism, from which the sample is removed, and/or other information, which concerns the sample, are entered automatically.

Data that are entered and made available by the device are indicated on a display. All such-entered data on the test capsule and organism and all other data relevant for the removal or processing can then be associated in such a way that the device makes available the possibility of associating the entered or automatically input serial numbers of the test capsules and the entered or automatically input information on the organism from which the sample was removed and other information concerning the respective withdrawal of the sample, and these data plus the information on the association of these data can be stored on a storage medium.

The handling of the removed samples is decisively simplified by the fact that the storage medium is rigidly installed in the device or can be separated from it. The device configures the means for data transmission in such a flexible manner that all requirements for flexibility and efficiency can be achieved sufficiently for the first time. Essentially, this is achieved by the fact that this device has an electronic unit by means of which all stored data and information on the association of these data can be transmitted in a wireless manner and, as the case may be, data can also be received in a wireless manner. In addition, one variant of the device can also make available an interface, by means of which a cable connection can be produced for purposes of data transmission from or to the device.

The device according to the invention defines for the first time the technical solution for requirements of registration of livestock that is essentially secure against falsification. The device is in a unique position to fulfill these requirements. This can be attributed to the essential novel features of the device and of the method and of the test capsules used in the device and method. For example, the method provides for the fact that the mechanism for triggering the device is blocked by another mechanism, which is released only by the prior entry of data or confirmation of data. In this way, due to the plausibility test conducted by the device with the data, a constraint for correct data entry exists. Coupled to the sample withdrawal, a labeling of the organism can also be introduced, which is comprised either of a) a simple color labeling , b) a self-adhering strip, c) an adhering badge or d) a device that is self-adhering or rigidly anchored in the tissue, which serves as a carrier of any one of the following:

a barcode, a readable and/or writable integrated circuit, a magnetic strip, a transponder, a transmitter, a numerical code, a letter code, or a comparable coding or information carrier system or a simple color labeling.

Thus, if data of an organism are entered incorrectly, and the sample is taken from another organism, one variant of embodiment makes available a mechanism, which releases the device only with the simultaneous receiving of the signal of a transponder.

The special properties of the method are also characterized by the essential use of special test capsules for the method. These are characterized by the fact that their components are suitable for the purpose of being used directly as the sample remover for the withdrawal of a biological sample. One component of the test capsule is used for the removal of a tissue sample by punching, shooting, scraping, pinching, knocking against [guided shooting], by tearing out hairs or conducting the motion of a biopsy needle. The loading of the device with the components of the test capsule is simplified by the fact that one or more identical components of such test capsules are linked together; the strips or rings of parts of test capsules that are formed can be loaded as units of more than only one of such parts of a test capsule into the magazine or into an analogous part of a device; the direction in which these strips or rings of several such units are loaded into the device is established by a labeling introduced only on one site of such a strip or ring, in such a way that the serial numbers of all such linked parts of test capsules are defined in a clear manner by only this one serial number. This is, of course, useful and thus a component of the essence of the method, only if the test capsule is characterized in that the serial number, which is introduced onto the strips or rings, is in a form that can be read automatically by a device provided for this purpose or can be read by the user himself and can be entered manually into a device provided for this purpose.

It is also necessary for several applications to introduce a labeling on the organism when the sample is withdrawn. This labeling will contribute to the security from falsification of the method. The test capsule has one or more parts, which can be separated in order to remain as a label in the tissue of the organism, from which the sample was removed. These components of the test capsule can produce an ear mark after the test capsule is joined, which mark can only be removed by leaving behind visible damage on either the ear mark or the animal. In addition, parts of the test capsule, which remain in the tissue of the animal from which the sample was removed, can have:

a barcode a readable and/or writable integrated circuit, a magnetic strip, a transponder, a transmitter, a numerical code, a letter code, or a comparable coding or information carrier system or a simple color or analogous labeling.

The reliability of the method against falsification is further increased by the fact that individual sample containers or several sample containers joined in a chain make available one serial number, which is introduced during production or later. Thus, it can be checked at any time whether a serial number from the system has been lost or in fact has appeared several times. In addition, if a test capsule has been opened again or access to its content has occurred after sealing by the test capsule cover, this can be accomplished only by leaving behind detectable changes. Thus, a falsification or exchange of the sample is no longer possible after a data entry and a sample withdrawal that is correct (thanks to the method).

The further processing of samples, which comprise processes in which the test capsules must be integrated as seamlessly as possible for purposes of greater efficiency is increased, in that the test capsule can have a site, which permits penetration by needles, pins, cannula or comparable devices, e.g., through a septum. This makes opening them unnecessary. Variants of the test capsule can also be characterized by the fact that parts of the test capsule are filled with reagents required for further processing of the sample. If it should be necessary to open the test capsules within another processing step for the removed samples, then the test capsule cover can have an extension for its easy removal from the test container on the side turned away from the sample, but of course, not without leaving behind traces on the capsule.

In general, the test capsule must be equipped with several properties provided in advance by the device according to the invention. For example, the sample-withdrawing part of the test capsule must have one or more slots, boreholes or recesses for receiving tissue on the side turned toward the sample. The following properties describe, however, only a few examples of possible variants of embodiment. The field of protection will apply to the more general and more essential properties and will not be limited by the following properties of the test capsules.

For example, as a sample remover, the test capsule cover may have a borehole, a slot, or the like for attaching a guide, on the side turned away from the sample. One embodiment variant of the method by means of the device also contains test capsules, which are characterized by the fact that the sample-withdrawing part of the test capsule has depressions on the side turned away from the sample, and these depressions can serve for the purpose of (a) pressing and squeezing the sample remover onto the tissue in such a way that a tissue sample can be removed by pinching, or (b) so as to advance obliquely and under pressure on the tissue so that a tissue sample is removed by scraping. The sample container cover may also, however, be slotted and partially conical, so that two or more tips can be easily pushed into it upon contact with the subject and then are pressed together due to the conical form, so that a small quantity of sample is sheared or cut and no other material is withdrawn.

EXAMPLES OF THE DEVICE

The invention concerns a method and devices with which biological samples are removed. Simultaneously with the removal of samples, an entry of data is made possible by means of an electronic storage unit. Possible configurations of the device for removing the sample are described in FIG. 1 and FIG. 2. The devices serve for bringing together two components of a test capsule (test capsule cover and sample container). The components of the test capsule are designed in such a way that sealing the test capsule leads to the fact that a tissue sample comes to lie inside the test capsule. Each sample is recorded by entering data for the sample. Several variants are proposed for the embodiment of the test capsule components. These variants make possible, e.g., the removal of a biological sample by punching out a tissue sample by pushing a part of the test capsule through the organism (FIGS. 3–5). In addition, a test capsule component can be "shot" through the organism (FIGS. 17–20). Another variant is that the test capsule component scrapes off a tissue sample from a surface, which subsequently comes to lie in the test capsule (FIGS. 10 and 11). A tissue sample can also be pinched off (FIGS. 7 and 8). Variants, which are similar in function to a biopsy needle are also possible (FIGS. 6 and 9). A preferred variant of the method concerns the recording of cattle, for which reason a simultaneous introduction of an ear mark is conducted with the removal of a biological sample, in order to prepare a genetic fingerprint (FIGS. 14–16, 25–26). It is described in FIG. 24 how the control or monitoring of a meat sample can occur by comparing the results of a genetic fingerprint of the meat sample with the genetic fingerprint of the animal.

The method and the devices make possible the removal of samples in very rapid sequence. Since the components of a test capsule are used only once, no problems occur with respect to contaminations and there is no need for sterilization. Safety from fraud is taken care of by the system, in that the removal of a sample is coupled with the direct entry of data for the corresponding animal. An incomparably rapid removal of samples is achieved by the automatic withdrawal of biological samples and the simultaneous recording. This also opens up possibilities for coupling with very rapid analytical methods. It is conceivable that a variant of the device, as it is shown in FIG. 1, can find application in emergency medicine and in the operating room, in order to be able to rapidly introduce tissue samples to a laboratory analysis. Other applications, which require a simple and cost-favorable withdrawal of samples, can be found in plant cultivation and plant quality-control. One embodiment of the device shown in FIG. 1 is applied to the method for withdrawing and recording biological tissue samples from leaves.

FIG. 1: A technical example of a mechanical fully automatic device for removal of samples in large numbers of units. The device essentially is comprised of a mechanical unit and an electrical unit. The mechanism of the device is based on the principle of "shooting" or "stabbing" or punching, whereby the actual advantage is characterized by the fact that the sample is removed with the sample cover and is joined in the same working cycle with the sample container to make up a solidly sealed test capsule.

This type of sample removal makes possible an absolutely contamination-free, as well as, simultaneously, a sterile withdrawal in the case of living subjects. The device introduced here as an example will be applied to the removal of samples from animals. Here, the tissue sample is removed by piercing the edge of the ear. The device possesses a firing pin 7, which receives its firing force from a firing spring found in the device. The firing force of the spring can be adjusted by the knurled nut 6. The adjustment of the spring thus makes possible a consideration of the resistance of the biological sample material relative to the piercing. By actuating trigger 12, the firing spring held under tension beforehand by pulling back firing pin 7 is released. The firing pin now impacts with the appropriately adjusted force onto a firing needle found in the device, in front of which a sample cover has been loaded by the tension of the firing pin by means of magazine 10 in handle 11. Due to the kinetic energy of the firing pin, the firing needle with the sample cover found in front of it is driven through the sample material and the sample cover containing the sample found therein is pressed into the sample container found in the sample magazine 3 and thus forms a solidly sealed test capsule in magazine 3 on counter-stay side 9. A restoring spring at the firing needle assures a subsequent immediate retraction of the firing needle from the test subject in order to avoid a lesioning due to the backward movement of the test subject. The container magazine 3 is shifted by one container position automatically by a mechanism for each renewed tensioning of the firing spring. Link 13 between the actual device and counter-stay 9 may be turned downward by 90° and makes possible, if necessary, a better accessibility of the device for inserting the tissue provided for the sample removal. The electronic unit integrated into the device fulfills another important aspect, and for example, consists here of an alphanumerical display 1, e.g., an LCD matrix display, a numerical or alphanumerical keyboard 2 for data entry and confirmation, a medium for data storage 5, e.g., a smart card with additional magnetic strip and a barcode reader 4. The particular features of the device thus form a meaningful combination of electronic unit and blocking mechanism for the mechanics for security [safety] purposes, in order to exclude a mixing up of the samples. The container strip to be inserted for loading into magazine 3 (FIG. 12) is characterized by a tab introduced on one side of the container strip containing continuous numbering by a barcode, which is read by means of barcode-reading pin 4 prior to insertion. The electronic unit of the device initializes smart card 5 which has been previously inserted into the card reader and stores the number of the barcode that is read in. The sample container strip (FIG. 12) can be inserted only in one direction into magazine 3 and loaded into the device. This permits only one defined removal sequence. After the device is loaded with the container strip, the electronic unit blocks trigger 12 and asks for the entry of a number clearly identifying the subject by means of the display. This number can be, for example, the breeding register number used for cattle. This number is entered by means of the keyboard. In addition, it is indicated on the display. After confirming on the keyboard, the latter is stored on memory card 5 for the first sample to be removed and the electronic unit releases the safety catch from trigger 12. Display 1 asks for the sample withdrawal. After the sample removal has been completed by the operator, the electronic unit blocks trigger 12 and the display asks for the confirmation of a successful sample removal. This question is confirmed by pressing a specific key on the keyboard or denied by pressing another key. This information is stored by the electronic unit of the device also on the memory card. After again retracing of firing pin 7 from magazine cover 10, a new sample cover is automatically loaded and container magazine 3 shifts by one sample container position and the process of electronic data entry or the release of the device described here begins again. The described routine is repeated until all sample containers contained in the sample container magazine strip (FIG. 12)—16 units here—are filled and the device must be loaded with new sample covers, a new sample container strip, as well as a new smart card 5. The sample container strips as well as the smart card can be loaded together or separately for further evaluation and analysis, e.g., by mailing to a laboratory, by the clear arrangement of data on the memory card due to the stored barcode and the barcode of the sample container strip. FIG. 2 shows a simple mechanism in a forceps-like form, which would be suitable, for example, for removing small numbers of samples and requires no direct data entry possibility. One possible application is the biological removal of samples from plants. The forceps essentially consist of four main components. The special feature lies in the particular configuration of the left and right forceps jaws 16 and 14. The right forceps jaw has a special receptacle pin for piercing the capsule cover. The left forceps jaw 16 is provided with a borehole, which is used for the uptake [receptacle] of sample container 17. The two halves 21 and 22 of the forceps simultaneously form the forceps handles and are joined together by the common rotation point 18. A spring 19 around the point of rotation 18 serves for again spreading the forceps apart. The special shaping of the two halves of the forceps as well as the joining to forceps jaws 16 and 14 makes possible a parallel closing and opening of the forceps jaws. To remove the sample, the forceps are equipped with capsule cover 15 and sample container 17. If biological sample material 67 is found between the two forceps jaws, the forceps jaws are parallelly closed by squeezing together the forceps halves. The sample is punched out from the sample material by capsule cover 15 and sample container 17 serving as the die. When the forceps are completely closed, the sample cover is joined with the sample container to form a solidly sealed test capsule with the sample contained therein. The opening of the forceps causes the pin of forceps jaw 14 to be pulled out from the sample cover. After the complete opening of the forceps, the test capsule joined together as a unit can be easily removed from the forceps jaw 16 for further analysis.

FIG. 3 shows a test capsule, which can remove a sample by punching, in that the sample container 22 serves as the die and test capsule seal 23 serves as the stamping unit. The sample container makes available a small recess 24 at the bottom, which serves as the possible puncture site for a cannula in order to introduce or remove liquids, for example. The test capsule seal makes available a sharp outer edge 25 on the bottom side, which [edge] will facilitate the shearing of the tissue and guarantees a minimal sample quantity by means of a depression 26. An undesired opening of a sealed test capsule is hindered by a round groove 27 in the test capsule container and the counter-piece adapting to it in the test capsule seal.

FIG. 4 shows a test capsule, which can remove a sample by shooting, in that the test capsule cover 28 is shot through the sample material by the device that belongs thereto and is collected by sample container 29. Test capsule cover 28 makes available a conically running tip, which reduces the resistance to material penetration and facilitates the introduction into the sample container, and makes available a cylindrical depression 30, in which the tissue sample is collected. The function of a snap results due to a sharp-edged groove 31 in the sample container and in the test capsule cover, in order to prevent an undetectable wrongful opening of a sealed test capsule.

FIG. 5 shows a test capsule, which can remove a sample by knocking against it (guided shooting), in that the test capsule cover 32 is thrust through the sample material by the device by means of a guide, which is joined with the guide by the extension piece 33 and the depression 34 at the back end of the test capsule. Depression 34 can also serve as a puncture site for cannula and extension piece 33 can be used also for the automated removal of the test capsule cover. The sample container 35 makes available a septum 36, which is comprised, for example, of an inserted piece of rubber.

FIG. 6 shows a test capsule, which can remove a tissue sample, in that the test capsule cover 37 with tip 38 is injected briefly and abruptly into the test subject, preferably with the use of a device, and is then again directly pulled out. Small quantities of the tissue to be investigated are attached to barb 39 and the test capsule cover including the tissue sample can be inserted into sample container 40 and sealed.

FIG. 7 shows a test capsule, which can remove a sample in a pinching or clipping manner. This is accomplished as follows: the test capsule cover 41 conducts a radial motion from the open to the closed state via the device belonging to it, which attaches the cover to extension 42. At the moment when the projection 43, which runs into a sharp tip and is found on the front side, is guided past, at the opening edge of sample container 44, a tissue sample is pinched off.

FIG. 8 shows a test capsule, which can remove a sample in a pinching or clipping manner, but with which an additional device can be dispensed with, if necessary. Sample container 45 and cover 46 belonging to it are comprised of one part and are joined together by means of link 47. Radial motion is made around the link and can be conducted by hand.

FIG. 9 shows a test capsule which has similarities to a biopsy needle. The sample-taking part 48, which is sealed on one side and has a cutting, oblique edge 49 on the other side, can either be guided through the material to be investigated with the use of the corresponding device or can be inserted into the test subject and then can be withdrawn again. After removing the sample, the sample-taking part 48 is introduced into a container 50 or sealed with a cover 51.

FIG. 10 shows a test capsule, which can remove a sample in a scraping or grating manner as follows: the test capsule cover 52 is rubbed by means of the device belonging to it or manually on a suitable surface of the test subject under a certain pressure. Tissue parts are then removed by the lamellae or teeth 54 and stored. The test capsule cover 52 furnished with sample material can then be introduced up to stop 55 in sample container 53 and thus can be solidly sealed.

FIG. 11 shows a test capsule, which removes a sample in a scraping manner, similar to FIG. 10, but with the difference that the sample cover 56, as a sample taker with scrapers 58 is advanced in a radial movement to the test subject and is inserted into sample container 57.

FIG. 12 shows a belt-like container strip with tab and barcode introduced on it.

FIG. 13 shows another possible assembly of the sample cover in rotation-symmetric form for the case when a drum magazine is used in place of the rectangular-shaft magazine.

FIG. 14 shows another example for the configuration of the sample container and sample cover in combination with a characterization mark automatically introduced when the sample is removed, e.g., with a transponder transmitter that is coded and integrated in the mark. For this purpose, a sample container 60, produced by the injection-molding process, is suspended at a disk 59, similar to a gear wheel with inner gearing 62 and joined with small cross-pieces 61, and this fulfills the objective of a shooting head FIG. 15 shows the respective counter-piece to FIG. 14 with transponder transmitter 66 and a hollow rivet-shaped extension piece. The cylindrical part of the extension piece possess a puncture in the form of a rotation-symmetric groove 65, in which gearing 62 of the shooting head engages and thus forms an integrated system. The capsule cover 64 is produced separately during the production and then inserted flush into the hollow part on the disk side, so that the two parts form one unit. An appropriate possible application for this combination of test capsule part and part suitable for labeling is found, for example, in the case of large-scale removal of samples for classifying cattle by a genetic fingerprint. The mark (FIG. 14, FIG. 15) with identification number automatically introduced during the removal of a sample via a transponder transmitter 66 makes possible the clear assignment between the animal and the sample. In addition, the mark could replace conventional ear marks in cattle, especially since the identification number of the transponder transmitter can be read out without contact.

FIG. 16 shows, in operating principle, how a fully automatic mechanical device such as is shown in (FIG. 1) or a simple mechanical device as is shown in (FIG. 2) could be applied. FIG. 16a shows the parts positioned in the device with the tissue for the sample removal lying in between. FIG. 16b shows how the [device shown in] FIG. 15 with a punch is punched through the tissue and engages in the counter-piece [shown] in FIG. 14 functioning as the rivet head, and in the same step, separates the actual sample container 60 from disk 59 and attaches it in the counter-piece. Tissue is obtained in the hollow part of FIG. 15 by piercing the test subject. In FIG. 16c, the tissue in the hollow part is guided by means of a smaller pin, which is guided by the punch, further out from the device and moves the sample cover 64 found in FIG. 15 through the hollow part of the mark (FIG. 15) and thus transports the tissue piece to sample container 60, and seals the latter at the same time with the sample cover 64 to form a solid unit. FIG. 16d shows the punch and pin again withdrawn from the device, as well as the labeling that is introduced with a possible coding 66 and the sealed test capsule with the tissue sample contained therein.

FIG. 17 shows a test capsule cover suitable for removing the sample, the particular feature of which is a deeply worked slot 68, whereby the front part of the sample taker is comprised of two half-round pieces 69, which run into a tip. The lower end of the slot is worked out as borehole 70. For the secure attachment in the sample holder, the sample cover posseses a groove 71, which is worked out as a depression, and thus the tissue to be investigated is not damaged unnecessarily.

FIG. 18 shows a test capsule cover, which corresponds in its function to FIG. 17, with the difference that this design makes available two blunt-ending slots 72, so that four pieces running into a tip are formed.

FIG. 19 shows another variant of embodiment of FIG. 17. Here, three slots 73 are applied, which are each worked out in trapezoid form 74, so that 6 parts running into a tip are formed.

FIG. 20 shows the [components of] FIG. 17 after the sample removal with the removed tissue 77, and after the sample remover 75 was introduced as the test capsule into sample container 67.

FIG. 21 shows in individual steps a) through f) the functioning of the sample-taker from FIGS. 17 to 19. In a), the sample-taker can be seen just prior to contact with the sample material. It is conceivable that the sample-taker was accelerated in some form and now possesses kinetic forces, or, e.g., is uniformly shifted by a guide rod from behind. It can be seen in b) how the tips of the sample-taker are pierced into the material and thus a certain quantity of material is introduced between them. The actual removal of the sample is given in c). The two halves of the sample-taker are pressed together by the two oblique pieces with sample material in between and now pinch off the tissue lying between them. It can be seen in d) that the sample-taker pushes the tissue through the tips that are pressed together without being able to take up any additional tissue. It can be seen in e) and f) that the sample-taker has again opened at the front due to the lack of pressure, and the sample that has been removed is released. The advantages of this method of tissue removal lie in the fact that the exact site of the sample removal is exactly defined also by penetrating the entire tissue and that the removed quantity of sample can always be kept constant.

FIG. 22 shows a portable data entry device with internal data storage unit. This device can be used, for example, as an additional module to the sample-removing forceps, as shown in FIG. 2, and thus a fully compatible unit results for more complex removal units, as shown in FIG. 1. The numerical or alphanumerical keyboard 79 makes it possible for the user to enter data, e.g., the breeding registry number in the case of cattle or other sample-specific data. The LCD display 78 permits the user to monitor the data input as well as to confirm it by means of keyboard 79. In addition, the LCD display guides the user through the procedure for inquiry and for data entry programmed in the data input device. The battery unit 81 is responsible for the current supply of the data input device and can be equipped as desired with batteries or storage batteries. The output of the internally stored data is produced via an interface 80 by plugging it into the base station. In addition, an electronic adapter can be coupled to the interface, which makes it possible to connect the data input device to the data output via a radio [cellular] telephone.

FIG. 23 shows the base station, which is operated with mains current by means of cable 83. A modem incorporated in the base station is joined via telephone cable 84 with a telephone outlet and makes possible the data transmission to another data base. The integrated loading device makes possible the loading into the data input device by means of storage batteries. The modem in the base station also permits the input of new data entry procedures for user-specific applications into the memory of the data input device as well as the testing of the device.

FIG. 24 shows a chart for explaining the detection of identity between the sample of the test subject (e.g. of the calf) and the sample of meat that is removed (e.g., from the meat packinghouse or from the meat-for-sale). The sample of the test subject, which was found in the sample container, was removed with the device. The test subject received from the device a labeling with a code. The data for the specific information of the test subject as well as the code of the labeling and the position of the sample container on the test strip are stored on a storage medium by the device and sent by mail to the database or transferred directly by means of modem via telephone or radio [cellular] telephone to a database. The test strip is sent by mail for analysis, is analyzed there, and the data of the analytical results are transferred to the database. The sample of meat that is removed passes through the same procedure. The database now makes possible the clear detection of identity of whether a meat product in reality corresponds or does not correspond to its declaration of the animal source.

FIG. 25 shows another example for the configuration of sample holder and sample cover in combination with a characterization mark that is automatically introduced when a sample is removed, as they are currently used for cattle with a coded transponder transmitter integrated in the mark. The sample container 86, e.g., produced in the injection-molding process, is attached by small cross-pieces 87 to disk 85. Disk 85 has an inner gearing 88 similar to a toothed wheel, which fulfills the purpose of a shooting head.

FIG. 26 shows the counter-piece belonging to the sample combination relative to FIG. 25 with transponder transmitter 92 and a hollow rivet-shaped extension piece. The cylindrical part of the extension piece has a puncture in the form of a rotation-symmetric groove 91, in which gearing 88 of the shooting head is engaged and thus forms an integrated system. The capsule cover 90 is separately produced during manufacture and then inserted flush into the hollow part on the disk side, so that the two parts form one unit. An appropriate possible application for this combination of test capsule parts and parts suitable for labeling is found, for example, in a large-scale withdrawal of samples for classifying cattle by a genetic fingerprint and the simultaneous characterization by means of ear marks and the corresponding entry in the breeding register. The marks that are automatically introduced when the samples are withdrawn (FIG. 25, FIG. 26) with identification number via a transponder transmitter 92 make possible the clear assignment between the calf and the sample. In addition, the mark could replace conventional ear marks in cattle, and in particular, the identification number of the transponder transmitter can be read out without contact.

The possible functional principle for (FIG. 25, FIG. 26) could be applied identically to the sample combination already shown and described in FIG. 16, such as, for example, in a mechanically fully automated device as is shown in (FIG. 1) or in a simple mechanical device as is shown in (FIG. 2).

EXAMPLES OF THE METHOD

One of the most timely applications of the process according to the invention is the first step in a process, which is being developed by the company Genom Analytik GmbH (GAG) Bremen, for registering and monitoring all livestock animals. The device to be patented is an important component of the process. A flow diagram of the process is shown in FIG. 24. The role of the device according to the invention proceeds from this.

A breeding association or another organization in charge of control of origin can order from the manufacturer of the sample containers according to the invention a specific quantity of sample containers, which are delivered labeled clearly with serial numbers. The manufacturer of the sample containers stores the serial numbers electronically indicating to whom these sample containers were delivered. A serial number can be, for example, 10 digits, which makes possible the production of up to 80 billion sample containers without duplicating a serial number (each serial number characterizes a strip of at least 8 containers). The controlling or monitoring organization obtains for itself or for the individual farmers or milk inspectors (this applies to Germany; other organizations are involved in control in other countries) a number of devices for the withdrawal of samples.

Equipped with these devices, the inspecting person of a region visits the farmer, who by law is obligated to report all births of calves. The breeding association assigns to each farmer, who has reported a birth, the corresponding herd book number, which is given to the person who withdraws the sample. The inspectors equipped with the containers, the device and the herd book numbers conduct the following process on each animal. The device is loaded with the sample containers and test capsule covers. In this way each sample container can be comprised of two components, the container itself and a part of an ear mark. In this case, the cover of the test capsule is also comprised of two parts, the cover itself, which simultaneously executes the sample withdrawal and another part of the ear mark. In a preferred process variant, the sample containers are supplied in the form of strips, or rings, on which several such containers are found. These containers are linked up into one strip in such a way that they cannot be separated from one another without obvious damage of the strip. The covers may be supplied either individually, in strips or in rings. Since these are separated from the strips or rings when the sample is removed, it is not necessary to supply them rigidly sealed with one another. If the covers are supplied as strips or rings, then this is done primarily for purposes of a simpler handling of the device during the loading process. One of the two parts of the ear mark can either be provided with a serial number (for example, the herd book number directly) or such a number can be given in the form of a transmitter or transponder. Now, if the device according to the invention with the sample containers and test capsule covers according to the invention is loaded with ear marks, the following occurs: the device automatically reads the serial number. FIG. 12 shows a possible variant of the container strip, in which a barcode is attached in the form of a "tab" on the strip, such that the loading direction is indicated. All other containers on one strip are clearly characterized by a number. The device requires the entry of a precise characterization of the animal. The device can be programmed in such a way that an entry that does not correspond to the correct form will immediately result in an error message. In this case, a sample removal cannot occur, since the device will not be released. The device can also conduct a plausibility test of the entry by other programs. For example, specific copies of the device, which are used only locally in a specific region, could only accept specific codes used only in this region. For example, it can be programmed that a device supplied in Germany only accepts herd book numbers with the characterization "DE" in order to release the device for sample withdrawal.

If the sample container and cover are jointly supplied with the parts of an ear mark, the device must be able to assign a clear characterization to each ear mark. A preferred example of embodiment would be such that one part of the ear mark is provided with a transponder. This bears the information for exactly one number, which is assigned the number of the container. The device can read this information and automatically carry out the assigning of the ear mark number to the serial number and the position of the sample container, which has just been loaded. This association can thus be combined for the mechanical release of the device for removing the sample. Thus a sample removal without simultaneous attachment of the ear mark is excluded.

The described process steps lead to the following situation. Information has been combined in the device on the precise characterization of the sample container, on the number remaining on the animal, and the herd book number, for example, assigned by the breeders' association. The information is stored by the device in such a way that it cannot be separated. Only if all of these steps are executed, will the device signal that now a sample withdrawal can occur. This can be produced by a light signal, an acoustic signal or other equivalent signal.

The actual sample withdrawal is conducted mechanically in the preferred variant of the device (FIG. 1). The device can be placed under tension prior to the sample withdrawal in various variants and then can be released by a trigger or can be actuated mechanically like a tacker, or the actual withdrawal can be driven by a motor. In one variant of the method, a sample strip is introduced up to a defined point in the device and then automatically a new cover (with label) is loaded after each sample withdrawal and the container strip is shifted by one position, so that the cover is found in line with a punching pin. The mechanical triggering thus has two consequences. The punching pin is introduced in the depression of the cover and, after entrainment of a tissue sample, is driven through the tissue into the container, and then is newly loaded after the backward course of motion of the punching pin with the two parts of the test capsule. The device is blocked for further removal of samples until a completely new set of information is entered. The punching of the cover into the sample container has as a consequence the fact that the latter is sealed so that it can no longer be opened without visible damage to the container. It is therefore assured that the tissue sample found in the container is associated in an inseparable manner with the herd book number and the ear mark number. The possibility of misuse is considerably limited in this way. Part of the further process is that the test capsule strips (containing tissue) will be inspected for damage. It is known to the manufacturer (and thus to the analytical site) which units the containers are delivered in. A separation of individual containers from a strip is obvious. After filling a complete strip of containers, the strip is removed from the device and can be shipped. The strips are therefore extremely robust, but flexible. The capsules are sealed in a water-tight manner, so that allowing them to fall by mistake into a puddle of water has no influence on the sample.

A milk inspector (in Germany) fills a number of test capsule strips in this way over a specific period of time. At regular intervals, the collected samples are packaged and shipped.

The transfer of the data, which can be stored in the device, can be conducted in different ways, each time depending on the organizational structure of the region, the country or the association. A preferred example would be the storage of the data on a smart card. A readable and writeable electronic chip, which can accept all information on a certain number of samples, can be found on such cards. If the capacity of the chip is exhausted, then the device blocks any further removal of samples. After the chip has been completely filled or a minimum number of sample withdrawals has been documented on the chip, the smart card may be removed from the device and can be shipped separately or together with the filled test capsule strips. In addition, the serial number of the device, information on the person taking the samples, and the precise calendar date of the sample removal can be stored on the chip. The chip can also be blocked by a confidential number [password], so that the lafter can be written on only by a registered device with the use of registered container numbers. In addition, each removal of the card from the device could block any further writing until a new release is authorized by the central analytical site. An additional control mechanism arises in this way.

Instead of the use of a shippable smart card, one of the following variants of the method may also be used. The device can make available an interface to a computer, by means of which the documented data on sample removals can be transferred. The device could make available a coding algorithm, which stores all data directly in a way such that they can be interpreted only by means of a corresponding code, which is known only to the central analytical site. In this way, any manipulation of the stored information is impossible, since its content cannot be deciphered. Even information on the date, the sample remover and other security codes can be stored simultaneously with the information on the samples, marks, herd book numbers and individual animals. Such a device does not permit the user any type of access to the data entered and generated in the device. All data can be transmitted by the computer to a receiving station by means of a modem connection. It is likewise possible to connect the device itself directly or via a corresponding cable connection to a telephone network. Any receiving station can then be selected by means of the numerical entry functions of the device. This can be conducted also directly by connecting the device to a wireless network. In this way, all data could be sent directly and at any time.

The data transfer via an Internet connection makes it possible to transmit data from very many parts of the world in a cost-favorable manner, either all data or only data on the sample container serial numbers used, to a central location, which can conduct a plausibility test for the entire system. A plausibility test would include in this way the condition that each device would send the serial numbers of the sample containers used at regular intervals. It can then be checked whether serial numbers appear twice or whether they are used at places for which they are not provided. Since only one central station (for example, the manufacturer) makes available the information of which serial numbers have been produced and in which series these will be produced in future (these can be nonconsecutive, or arranged according to a secret system), an extended protection of the method against manipulation or falsification of the containers is present. There is limited possibility for breaking the system's security against falsification.

Example for Registering Cattle

The described device for the withdrawal of biological samples is prepared by entering the data of the calf, from which the sample will be taken, via the keyboard field in the device. In this way, the device is then released for withdrawing the sample. The tissue sample is removed from the calfs ear by shooting with the device with the simultaneous leaving behind of a mark. A data storage device (numerical and letter code, barcode, transponder or smart card) is found on the mark. These data are introduced with the entered data. After removing samples from several different calves, the belt with the test capsules is removed from the device and sent to the site of analysis. There, a genotyping of the DNA of the sample is conducted. This can be carried out by means of mass spectrometry or conventional methods. The genetic fingerprint is introduced into the herd book.

Example for Registering Horses

The described device for the withdrawal of biological samples is prepared by entering the data of the horse, from which the sample will be taken, into the device by means of the keyboard field. In this way, the device is then released for taking the sample. Several hairs are torn out by the device (by a gentle. brushing of the horse). The device transfers the hair roots into the test capsule. After removing samples from several different horses, the belt with the test capsules is removed from the device and brought to the analysis site. A genotyping of the DNA of the samples is conducted there.

Example for Registering Swine

The described device for the removal of biological samples is prepared by entering the data of the swine, whose samples will be taken, on an official form with a corresponding code (barcode) for that on the test capsule belt. In this way, the device is released for removing the samples. The tissue sample is removed by punching with the device with the simultaneous leaving behind of a mark. A data storage unit (numerical and letter code, barcode, transponder or smart card) is found on the mark. After removing samples from several different swine, the belt with the test capsules is removed from the device and brought to the analysis site. A genotyping of the DNA of the samples is conducted there.

Example for Removing Tissue in Humans

Prior to the excision of a malignant tumor, the surgeon takes tissue samples of the tumor and the surrounding tissue with the described device. The device for this case is constructed such that the tissue is taken and cut off with a knife mechanism. The knife instrument is sealed to the test capsule. It may be important to introduce reagents for further processing in a part of the test capsule (e.g., proteinase K in order to break up intact cells and to digest proteins). At the same time as the tissue is removed, a number is sprayed at the site of the respective sample removal (ink jet) by the device, or another labeling is left behind at the place where the specimen was removed. The samples found in the belt-type test capsules are introduced to a rapid analysis, e.g., genotyping by means of PCR in a microsystem and a time-of-flight mass spectrometer. Within 15 minutes, the surgeon receives his analytical results and can now decide how much tissue around the tumor has already been affected by the cancer cells. It is thus possible for the first time to keep plastic damage of an excision as small as possible.

Example of Embodiment in the Field of Marker-supported Plant Cultivation

A crossing of a wild type with a useful [food] plant has the purpose of transferring to the food plant the genes that the wild type has for a desired property, e.g., a resistance to pests. It is known that the resistance is transferred by several genes of the wild type. For the most part, only genetic markers are known, which lie on the chromosomes very close to the corresponding genes, but not the genes themselves, or their precise site in the genome of the plant. These genetic markers are present in several alleles (molecularly different versions of the same marker can occur in various individuals). It is known which versions of the markers "coupled" to the genes are present in the wild plant and in the food plant. Several hundred different markers of wild and food plants are known and can be utilized for cultivation.

A crossing of the wild plant with the useful plant produces a population of thousands of plants, only a few of which contain the desired combination of markers and thus of the genes. Also, these plants have individually different percentages of genes of the wild plants. The wild plants often bear a number of "troublesome" properties, such as smaller yield or smaller stress capacity under dry conditions. Now, plants must be identified that contain the smallest proportion of the genome of the wild plant, excepting those sites in the genome responsible for the resistance. Only these plants will then be propagated further in the next generation.

The method according to the invention would solve this problem, for example, in the following way.

The device is designed in such a way that a small (<1 cm diameter) flexible plastic mark with a consecutive number is stamped through the leaf from which the sample is removed, with each withdrawal of sample. The plastic mark can also be glued by hand in the removal process instead of this (depending on the quantity of samples). The removal device counts each sample withdrawal, and thus at any time has knowledge of the consecutive numbers and can indicate these in a display. When the attachment of the label is not automatic, the operator can check at any time to determine whether the number which is (or was) attached also corresponds to the number which the removal device assigned to the respective sample container. Since the sample remover is a part of the test capsule, each removal takes place in such a way that no material is entrained from other plants, which may contaminate the subsequent highly sensitive analyses. Sample container and sample remover are delivered in this variant, for example, as long chains of individual units or in magazines and are loaded into the device prior to beginning the operation. In this way, large quantities of samples can be taken one after the other in the free field without a new loading of the device. The actual sample removal is now conducted in such a way that the operator introduces a leaf into an intermediate space in the device which is provided for this (only the device moves, thus guided by hand) and when the device is triggered, punches the sample cover through the leaf into the sample container. The cover entrains a defined quantity of the leaf tissue, which comes to lie directly in the sample container sealed by the process.

The filled test capsules can be removed from the device directly, for example, in unit quantities to be established, and collected in a carrier bag. It is also possible to store these directly in the magazine (which can be a drum magazine). A coding is attached to a place on the supplied sample container unit. This means that if sample containers are supplied in 24 units (e.g. strips of 24 containers chained rigidly to one another), a serial number, whose position on the strip also indicates the direction by which this strip must be introduced into the device, is given, which clearly characterizes the 24 subsequent vessels. The serial number is of such a type that a user does not punch the same number twice during one application with a probability limiting on safety.

In the application example, this means that a huge quantity of sample containers will be centrally collected after the unequalled rapid withdrawal and labeling of the samples. These are present now in 8, 16 or 24-piece strips, which are aligned by hand to the serial number, and are distributed in 96-well or 384-well microtiter plate format. This format is standardized in molecular biology. The serial numbers of the strips can be read automatically. Thus, an analytical device now "knows" precisely where a specific sample is found in the microtiter plate.

The data of the plants (in this simple case, the number with which the plant was labeled, but also any other information as desired, such as, for example, the location of the plant) are found first still in or with the device. One variant is that the device is connected to a computer by means of a cable, which controls the analytical device or evaluates the data according to the analysis. The data are played over an interface present in the device to a computer. The computer can now assign to any sample stored in the 96 or 384-place format precisely the information corresponding to it.

After the analysis, which is conducted centrally, the objective is to determine precisely the number (and thus the location) of plants, which correspond for the most part to the desired genotype. In the case when the number is introduced by the device, no manual intervention has occurred in the transfer of data during the entire process. The sensitivity to error and the expenditure of labor are thus minimal with such a method. The described solution by the proposed method with the corresponding device thus means a reduction in cost.

Example Relative to Epidemic Control in Useful Animals

In the future, despite all controls, infectious diseases will propagate in livestock. In any case of disease such as BSE, in which the meat of infected animals must be kept out of the food supply, a rapid testing of a huge number of individual samples is necessary. In addition, in times of epidemic, imports and exports of livestock should be inspected. This means that customs and border control personnel must be able to take samples of large numbers of animals and to record these and send them for analysis without large expenditure of administrative time. A precise control, however, must not be protracted, since delays would lead to economic losses of animal breeders due to the perishable nature of the goods involved.

A situation in which the method according to the invention would be useful would be the situation that was experienced at the end of the '80s in Great Britain as a real threat. The entire livestock of an entire country (and this would involve a much greater number if this occurred on European soil or the continent as referred to by Americans) had to be tested for a disease within an extremely short period of time. Each sick animal could have as a consequence many casualties; on the other hand, neither can the utilization [marketing] of livestock be stopped nor can all animals be slaughtered in the emergency. In the case of the Federal Republic of Germany, this would mean the testing of large parts of an inventory of 60 million cattle. For swine or poultry, these numbers would be still higher. At the present time, rapid tests for BSE are being developed with highly promising results; and there are such detections for other dangerous diseases. In the indicated case, a large-scale testing of the animal stock would founder, primarily due to the logistics of taking samples and administering this process. Tests are useful, if they accurately identify the infected animals. The proposed method can resolve this problem. If, for example, one equips the large number of veterinarians with one device each and gives them a stock supply of sample containers for such cases, then such a complete "screening" can be conducted practically without additional logistic or administrative work. It must only be assured that each commissioned veterinarian has a specific region of responsibility and that every estate with a herd of cattle falls into the region of responsibility of such a veterinarian. Such regions of responsibility have already been regulated for a very long time for most herds by the existing laws. In the case of an epidemic, the veterinarians must be instructed to take a sample of all animals in their region or regions of responsibility in the shortest possible time. The variant of the device would thus approximately correspond to the one that is shown in FIG. 1. The tissue sample also contains enough blood in order to be able to essentially replace the more expensive sampling of blood in practically all cases. The veterinarian must enter the code of the respective animal prior to withdrawing a sample. In the case of the most advanced, preferred variants of the method, this code would be read in automatically on the basis of the ear mark (which contains a transponder) left behind in the initial withdrawal of samples (for preparing a genetic fingerprint). A particular advantage of this variant is that a sample can only be removed if a signal of a transponder is received simultaneously with the removal of the sample. This signal clearly identifies an animal and is assigned to the test capsule by the device together with all other relevant data, without the user being able to influence or avoid this. Thus the situation can be excluded that the herd book number of a sick animal of a herd is read in, but then the sample of another, in this case a healthy animal, is withdrawn. An essential advantage of the device is the combination with the test capsules according to the invention. By use of sample removers that are used only once, the risk of a transmission of disease is minimized. The sterilizing of a device is very time-consuming and must be carried out very conscientiously. The device according to the invention resolves these problems in a very simple manner.

In a crisis situation, hundreds of samples can be removed daily by one veterinarian, without the necessity for inscribing or sorting any samples. At the end of a day, the samples can be shipped to a central analysis station. The data for the samples are either shipped to a storage medium that can be separate from the device, together with the test capsules, or can be transmitted directly by telephone or Internet. In each case, the samples can be directly and fully automatically integrated into an analytical process in the central laboratory. In addition, the association of the results with the samples and thus the infected stocks can be conducted fully automatically. Apart from the reliable removal and analysis, the process according to the invention also offers an efficient tool for epidemic control. By an extremely rapid flow of data in electronic form, epidemic foci and paths of propagation are identified, which are a prerequisite for combating the epidemic and thus minimizing the damage.

BRIEF DESCRIPTION OF THE FIGURES

FIG. 9. Test capsule, which can remove a tissue sample a biopsy.

FIG. 10. Test capsule, which can remove a tissue sample by scraping.

FIG. 11. Test capsule, which can remove a tissue sample by scraping.

REFERENCE LIST

Figure 1:
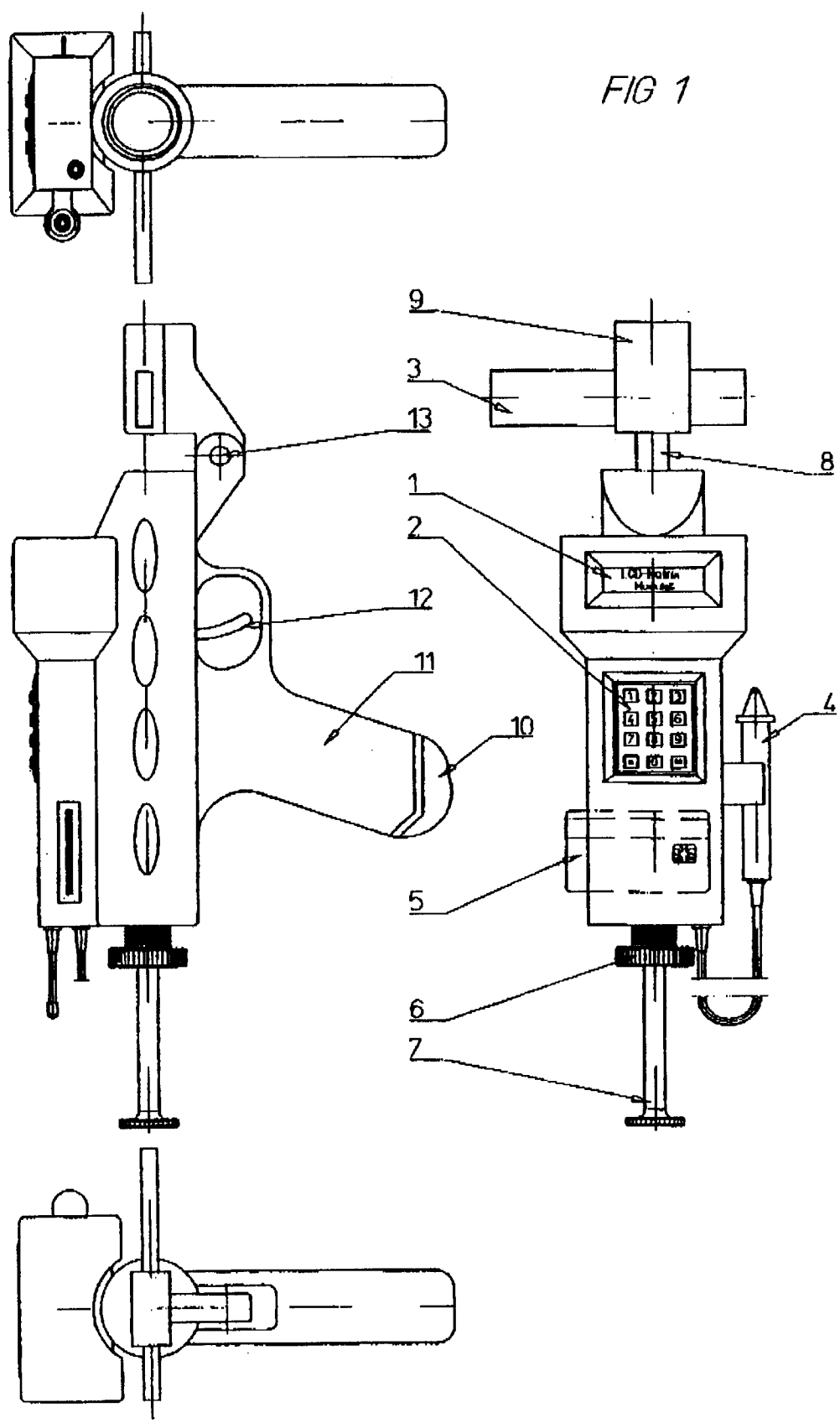
FIG. 1. Fully automatically operating device for the withdrawal of biological samples. The device brings together two parts of a test capsule after a data entry, with the removal of a tissue sample. Test capsules are formed as belts. Each test capsule belt has a tab with a unique code. This code is read by the device for recording and the data are entered.
Figure 2:
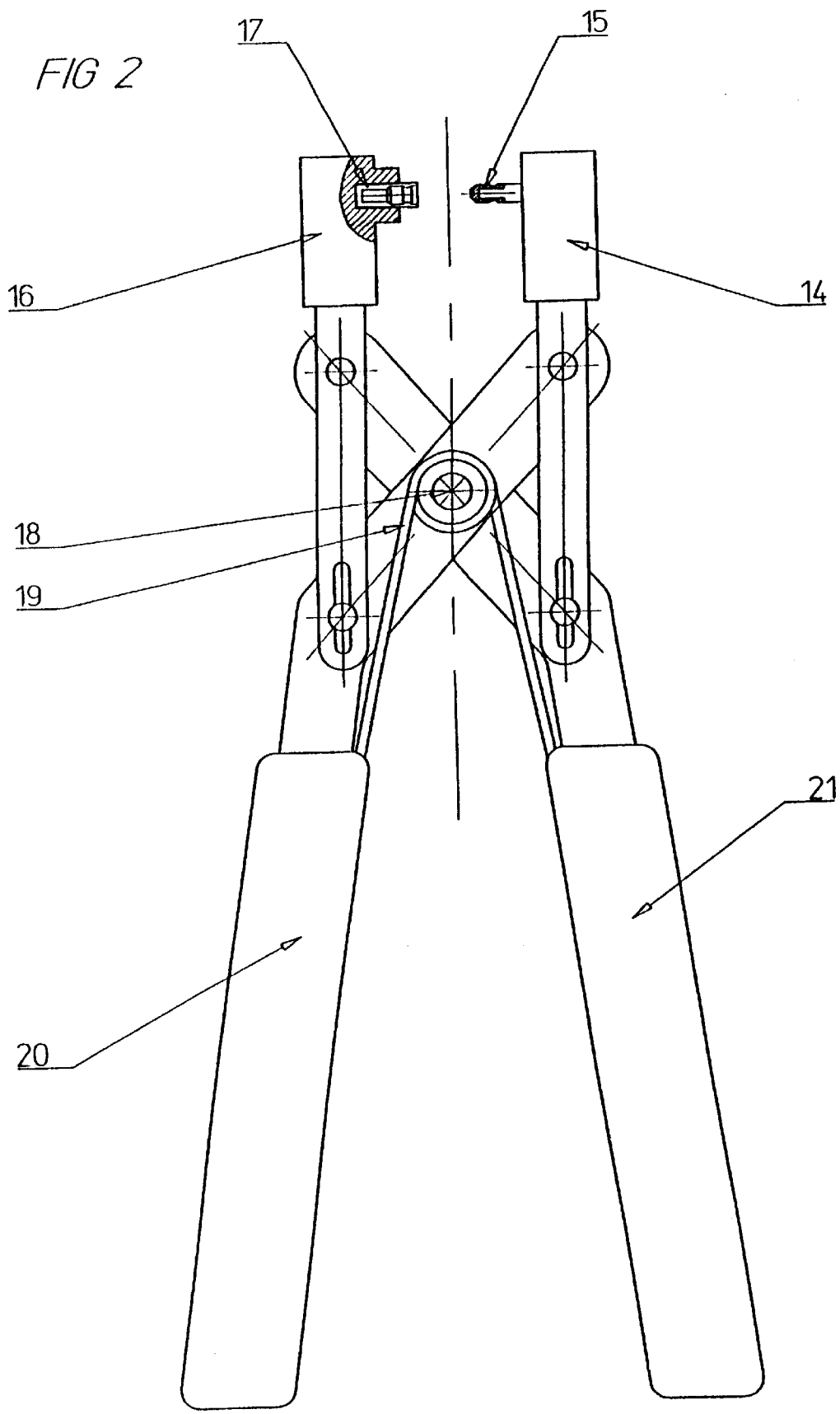
FIG. 2. Simple mechanical design of a device for withdrawal of biological samples.
Figure 3:
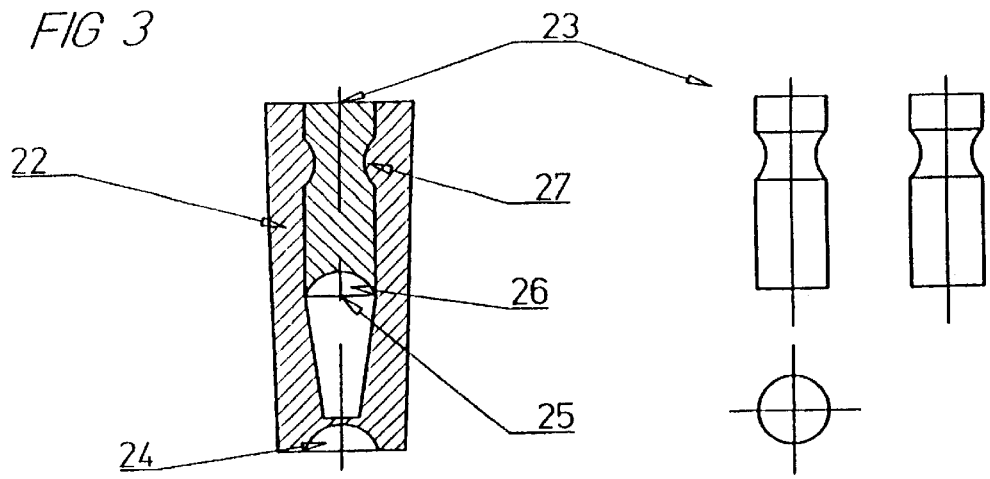
FIG. 3. Test capsule, which can remove a tissue sample by punching.
Figure 4:
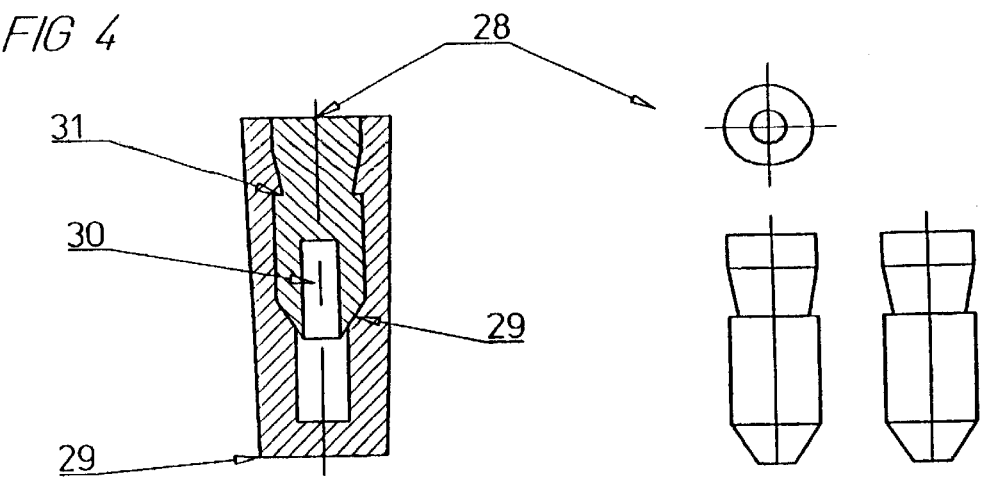
FIG. 4. Test capsule which can remove a tissue sample by shooting.
Figure 5:
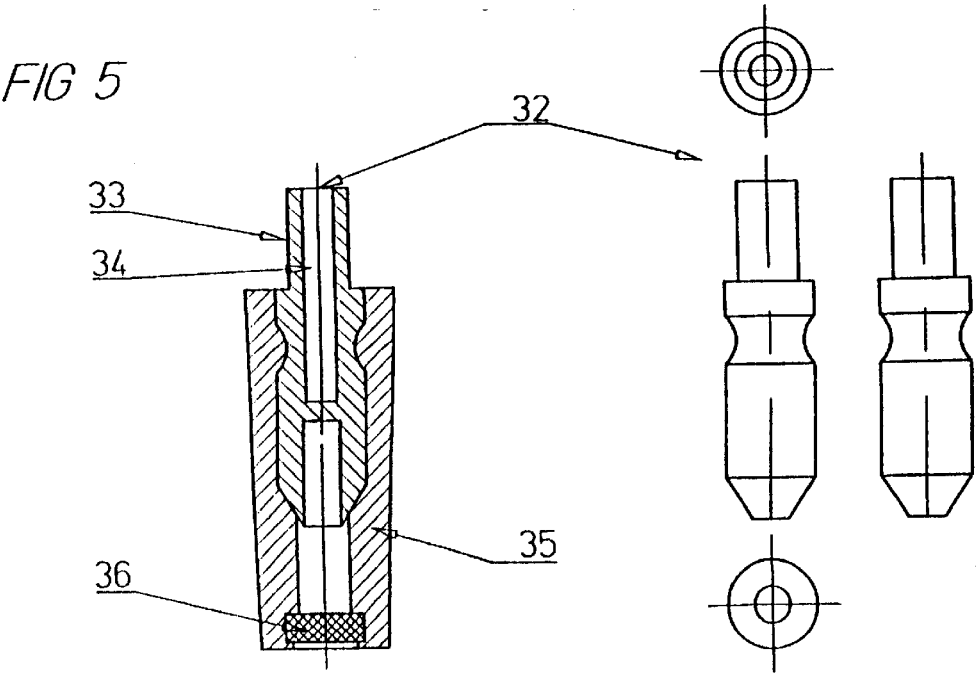
FIG. 5. Test capsule, which can remove a tissue sample by guided shooting.
Figure 6:
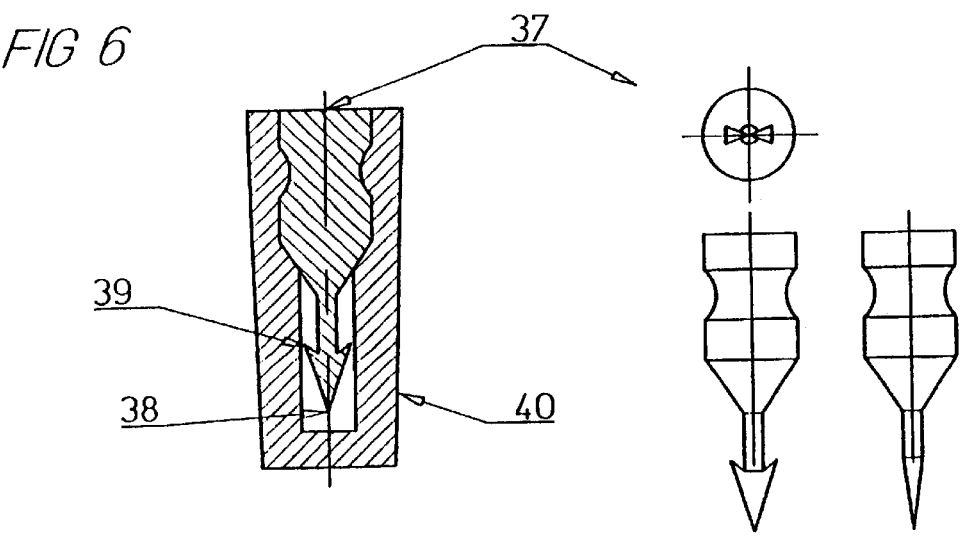
FIG. 6. Test capsule, which can remove a tissue sample by piercing.
Figure 7:
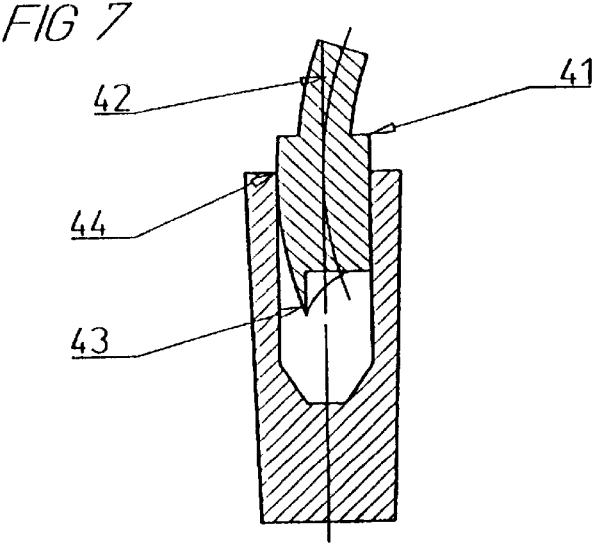
FIG. 7. Test capsule, which can remove a tissue sample by pinching.
Figure 8:
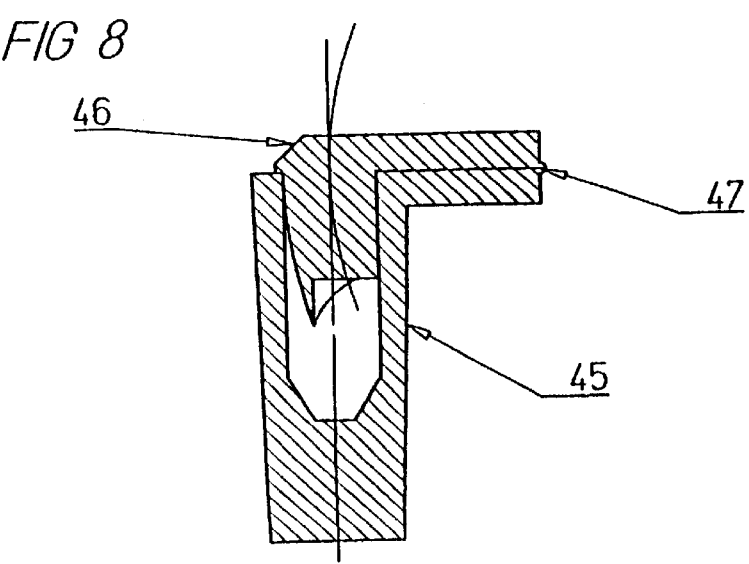
FIG. 8. Test capsule, which can remove a tissue sample by pinching.
Figure 12:
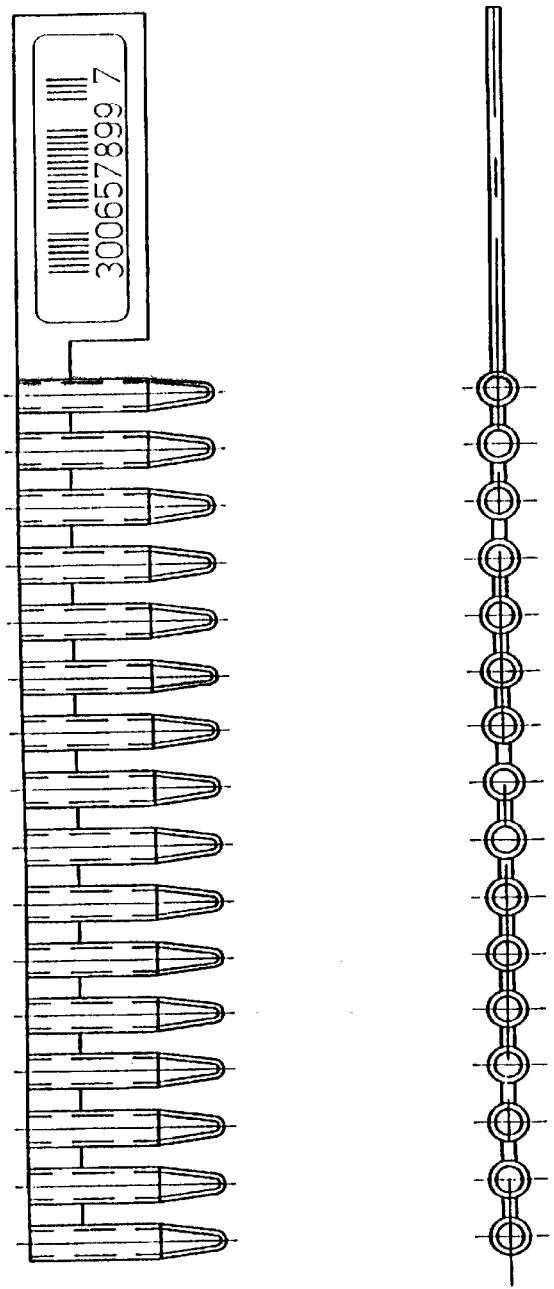
FIG. 12. Belted strips of sample containers.
Figure 13:
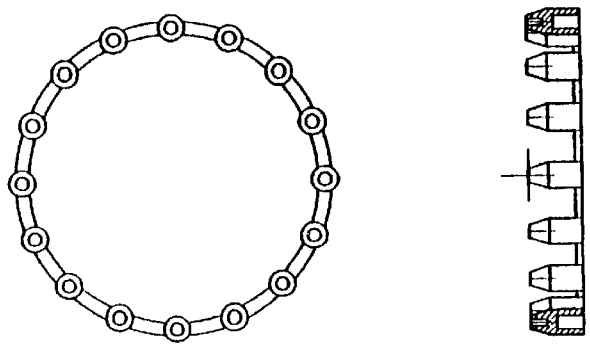
FIG. 13. Sample covers in rotation-symmetric form.
Figure 14:
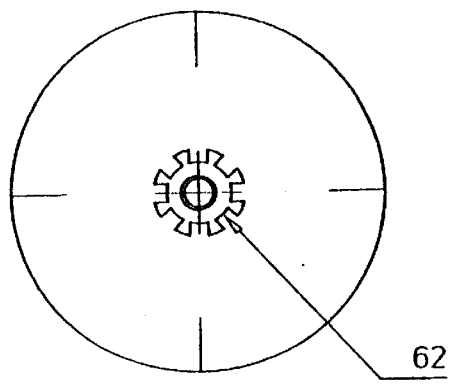
FIG. 14. Configuration of sample containers and sample covers, with which a tissue sample can be removed and an ear mark can be introduced simultaneously.
Figure 14:
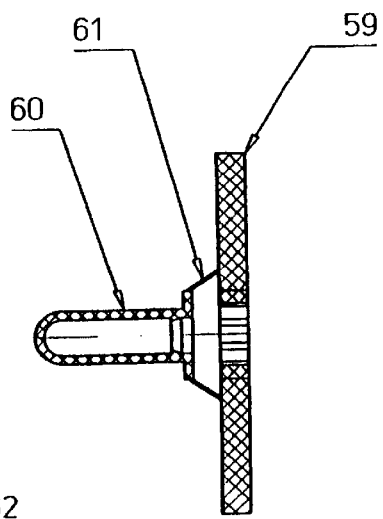
Figure 15:
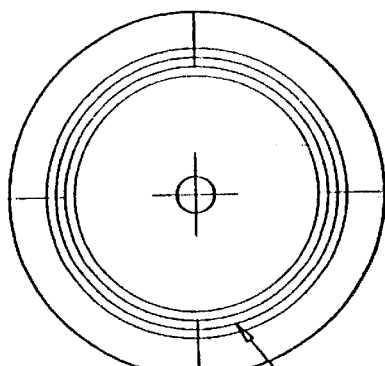
FIG. 15. Counter-piece belonging to FIG. 14.
Figure 15:
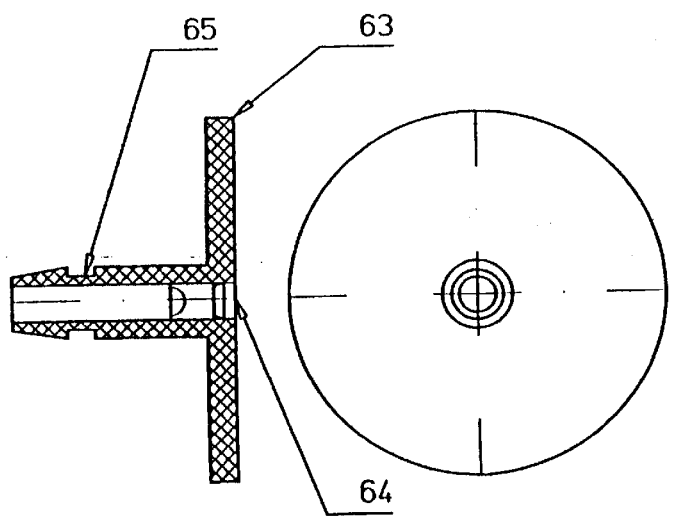
Figure 16:
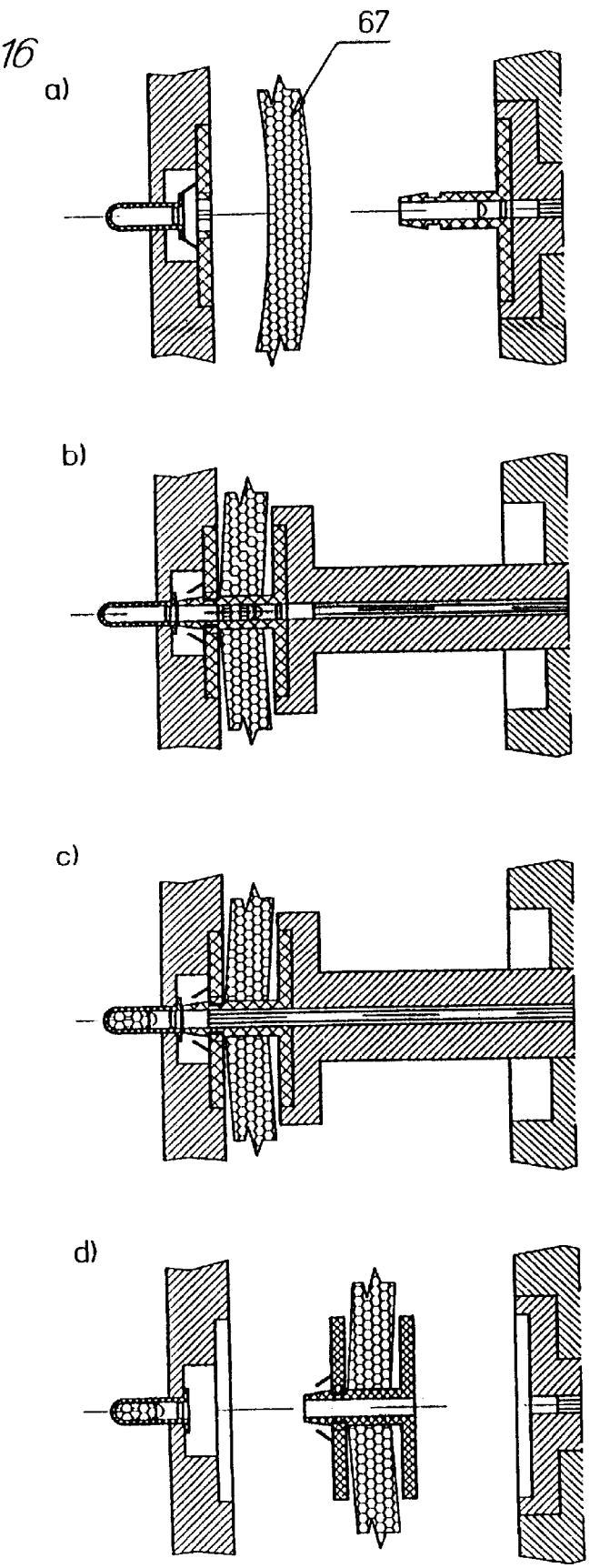
FIG. 16. Functional principle for the removal of a tissue sample from a calfs ear with the simultaneous introduction of an ear mark.
Figure 17:
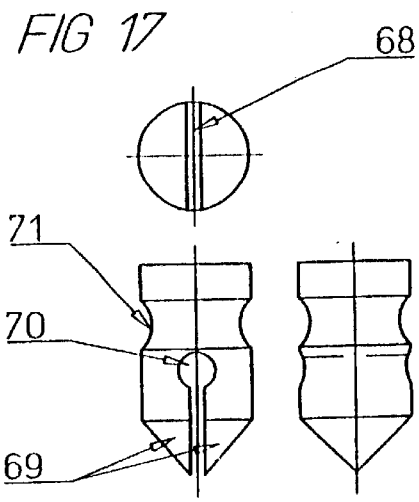
FIG. 17. Test capsule cover, which first removes a sample during motion through the tissue, then forms a sharp [closed] tip, and the additionally penetrated tissue is damaged as little as possible.
Figure 18:
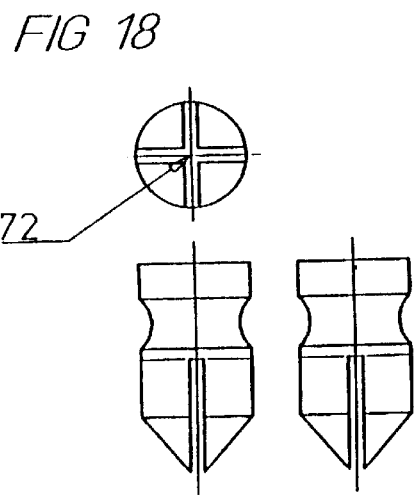
FIG. 18. Variant of FIG. 17.
Figure 19:
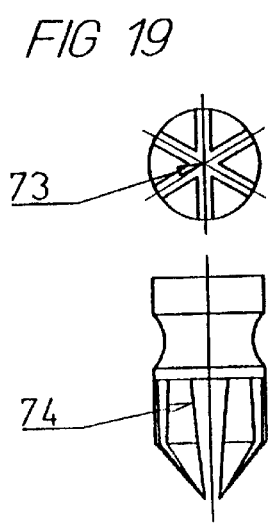
FIG. 19. Variant of FIG. 17.
Figure 20:
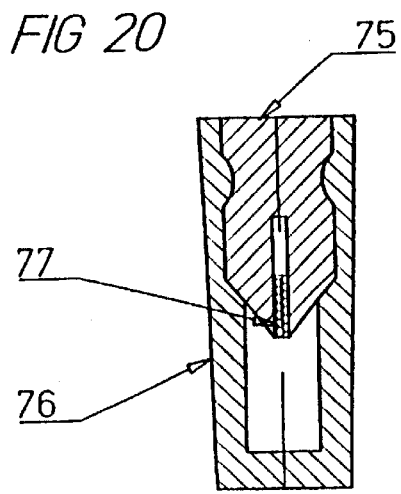
FIG. 20. Test capsule cover of FIG. 17 after the removal of a tissue sample into the test capsule belonging thereto.
Figure 21:
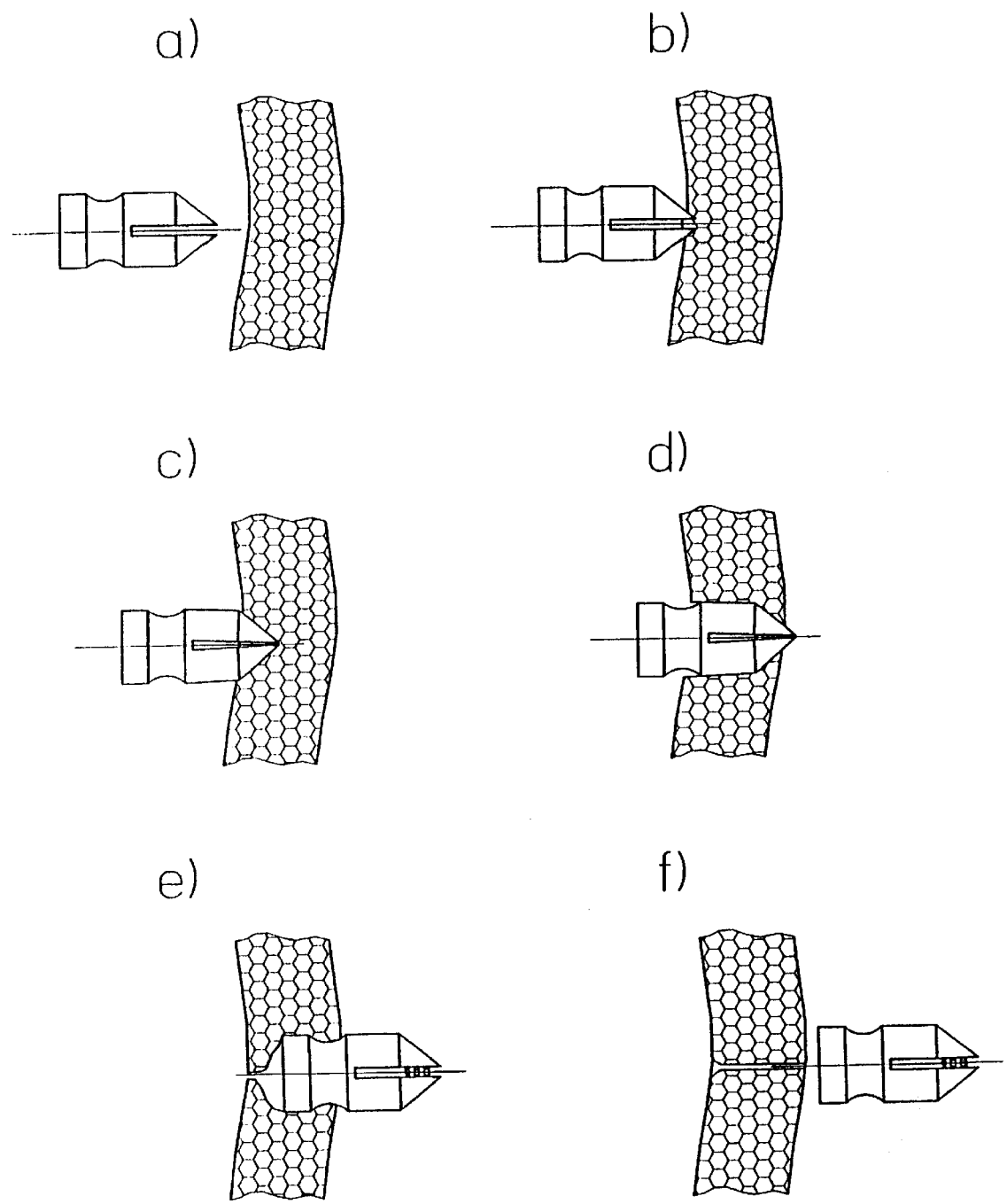
FIG. 21. Functioning of the test capsule cover of FIG. 17.
Figure 22:
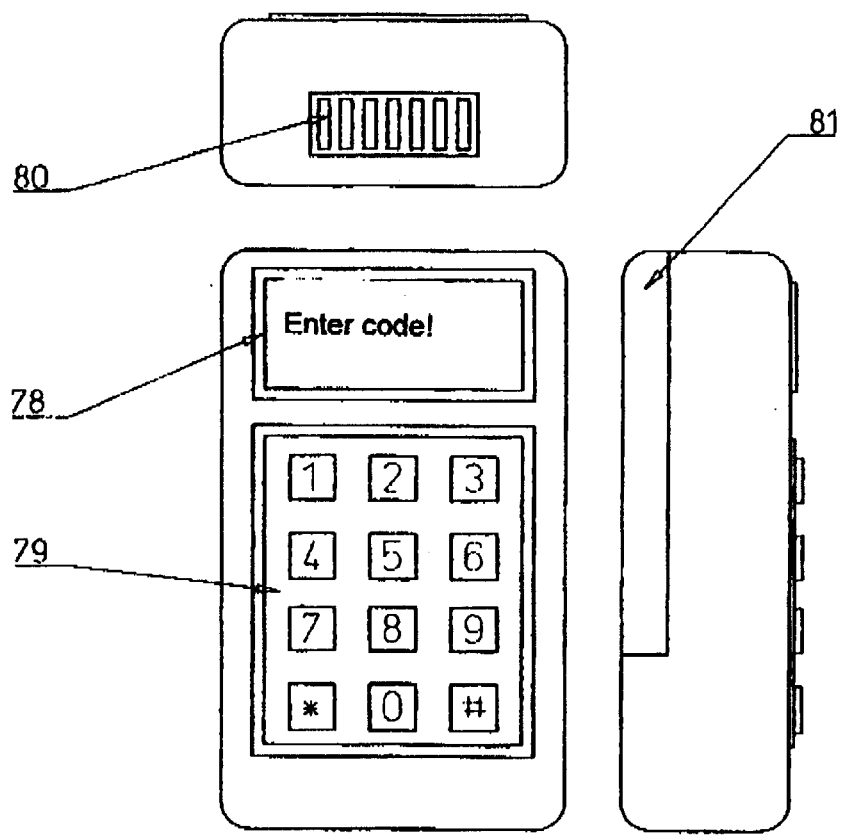
FIG. 22. Portable data entry device as an additional module to a sample removal device as shown in FIG. 2.
Figure 23:
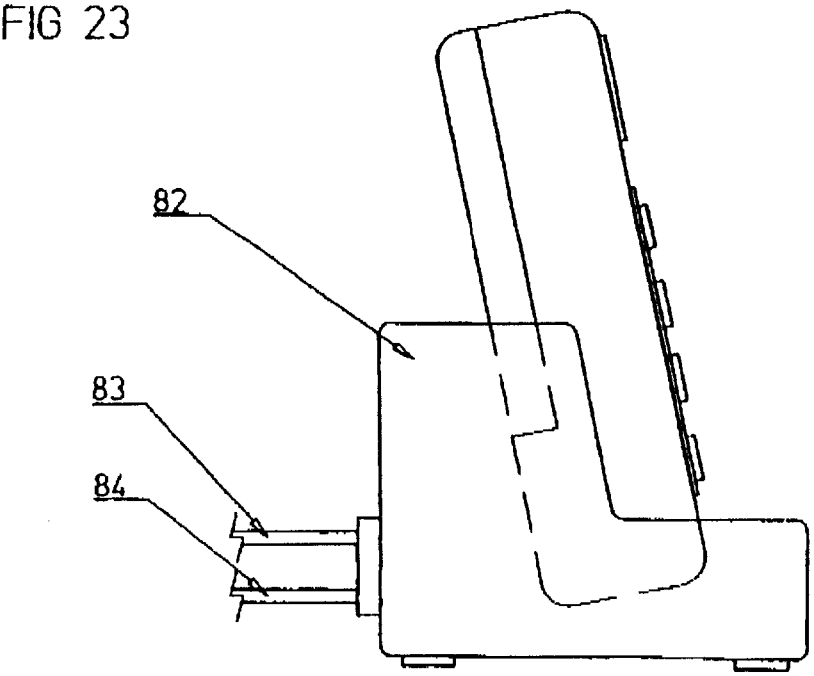
FIG. 23. Base station for the data entry device of FIG. 22, with which data can be transmitted.
Figure 24:
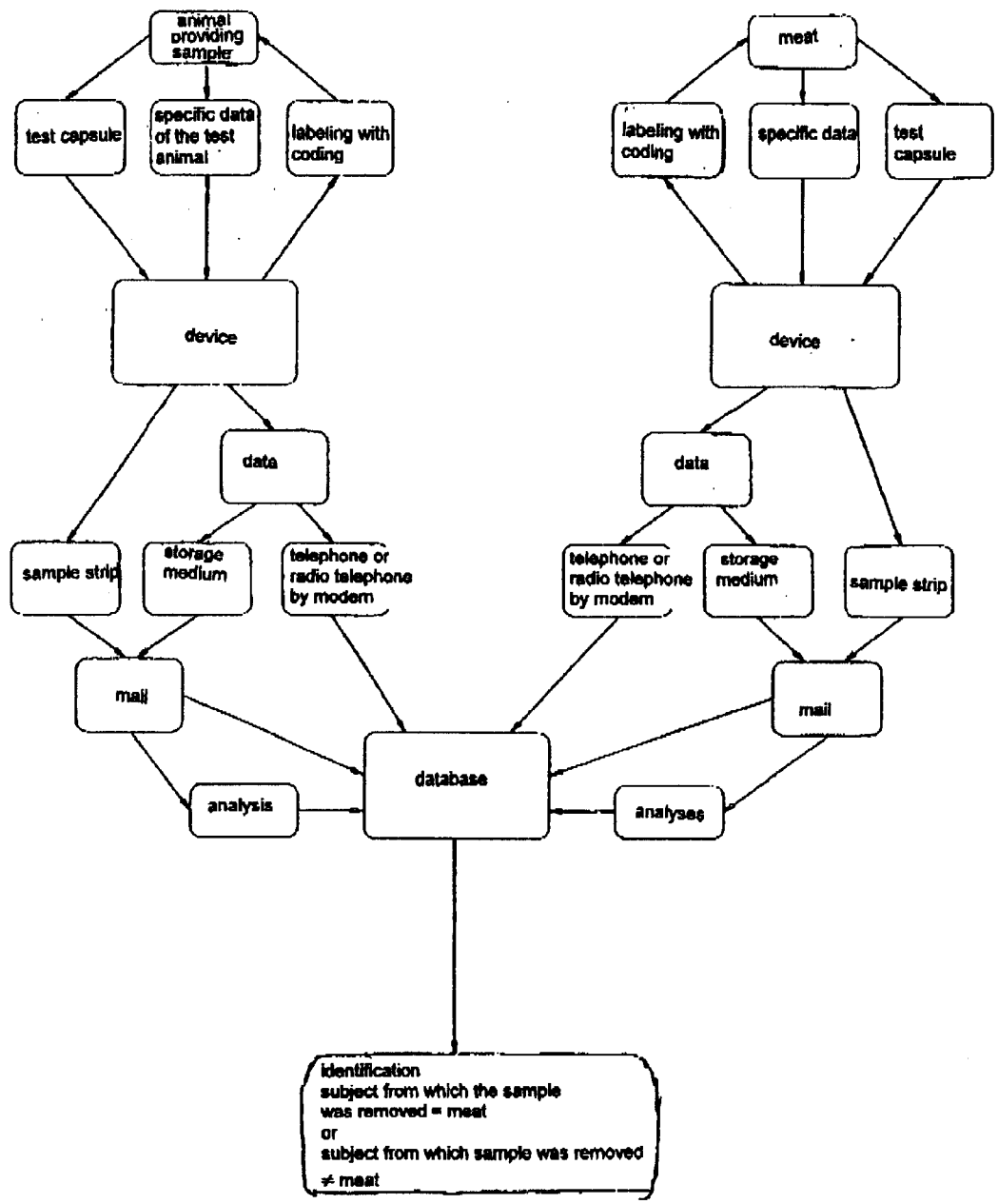
FIG. 24. Flowchart for the method of detecting the identity of a meat sample.
Figure 25:
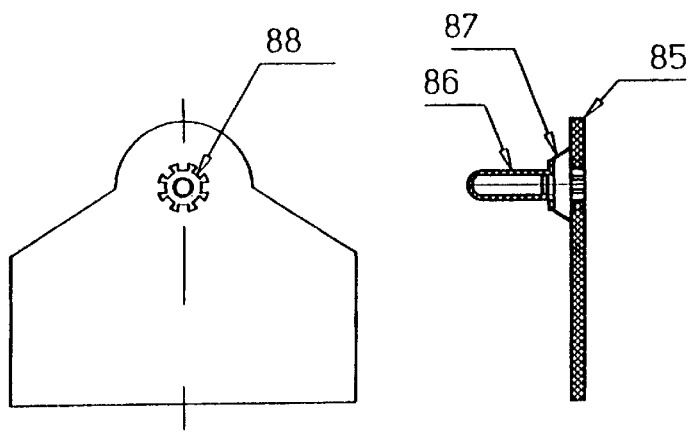
FIG. 25. Sample container and sample cover in combination with a characterizing mark automatically introduced when a sample is removed, as it is used at the present time for cattle. A coded transponder transmitter is integrated in the mark.
Figure 26:
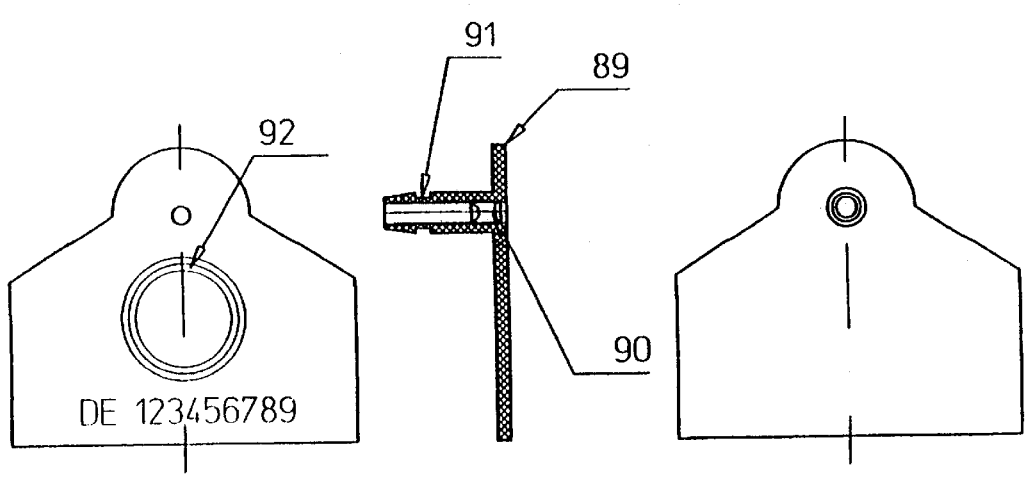
FIG. 26. Counter-piece corresponding to FIG. 25 with transponder transmitter.

1 LCD display
2 numerical or alphanumerical keyboard
3 sample magazine for containers
4 barcode reading pin
5 smart card
6 knurled nut
7 shooting pin
8 intermediate space
9 counter-stay
10 magazine cover
11 handle
12 trigger
13 link
14 forceps jaw with pin
15 sample cover
16 forceps jaw with borehole
17 sample container
18 point of rotation
19 spring
20 left forceps handle
21 right forceps handle
22 sample container
23 test capsule seal
24 recess
25 sharp outer edge
26 depression
27 groove
28 test capsule cover
29 sample container
20 depression
31 sharp-edge groove
32 test capsule cover
33 extension piece
34 depression
35 sample container
36 septum
37 test capsule cover
38 tip
39 barb
40 sample container
41 test capsule cover
42 extension piece
43 projection running into tip
44 sample container
45 sample container
46 cover
47 link
48 sample-taking part
49 cutting edge
50 sample container
51 cover
52 test capsule cover
53 sample container
54 lamellae or teeth
55 stop piece
56 test capsule cover
57 sample container
58 scraper
59 disk with inner gearing
60 sample container
61 cross-piece
62 gearing
63 disk with cylindrical extension
64 sample cover
65 groove
66 transponder 67 sample tissue (ear)
68 a slot
69 half-round piece
70 borehole
71 groove
72 two slots
73 three slots
74 trapezoidal
75 sample taker
76 sample container
77 removed tissue
78 LCD display
79 keyboard
80 interface
81 battery unit
82 base station
83 mains cable
84 telephone cable
85 disk or mark with inner gearing
86 sample container
87 cross-piece
88 gearing
89 disk or mark with cylindrical extension
90 sample cover
91 groove
92 transponder

What is claimed is:

1. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the device makes available a mechanism, which punches or shoots a component of a test capsule by means of a type of firing pin through the tissue, after placement of the device on tissue and actuating the trigger mechanism, in such a way that a tissue sample is removed on the path through the tissue and the sample remover is brought together with another part of a test capsule in the same course of motion to produce the closed test capsule.

2. A device according to claim 1, further characterized in that
   the part of the device bearing the sample container and the part of the device bearing the test capsule cover can be pressed together in such a way from opposite sides solidly onto the tissue, such that a mechanism found on one of the two sides can use a part of the test capsule for a sample removal, and
   the pressure thus exercised and the distance between the part of the device bearing the sample container and the part of the device bearing the test capsule cover can be regulated by an adjusting screw or analogous device.

3. A device according to claim 1, further characterized in that the device makes available a mechanism, which moves these components of a test capsule, by actuating a trigger mechanism jointly within the magazine, by one position in the direction of a sample-removing mechanism of the device.

4. A device according to claim 1, further characterized in that the device makes available a possibility for data entry and/or for data output or is coupled to such a device.

5. A device according to claim 1, further characterized in that the device makes available a mechanism and/or electronic unit, by means of which, data such as the serial number of the sample container or several sample containers linked together and/or information on the organism, whose sample is removed, and/or other information, which concerns the sample removal, are read in automatically.

6. A device according to claim 1, further characterized by the fact that the device comprises a receptor to hold one or more covers for sample containers.

7. A device according to claim 1, further characterized by the fact that the device comprises a receptor to hold one or more sample containers.

8. A device according to claim 1, further characterized in that the trigger mechanism is blocked by another mechanism, which is released only by the prior input or confirmation of data.

9. A device according to claim 1, further characterized by the fact that the device makes available a mechanism, which joins the test capsule cover and the sample container in one working cycle with the removal of a biological sample either by the test capsule cover or by the sample container to form the test capsule.

10. A device according to claim 1, further characterized in that one of the components of the sample capsule is suitable for the purpose of being used directly as the sample remover for removing a biological sample.

11. A device according to claim 1, further characterized in that one component of the test capsule is used for removing a tissue sample by punching, shooting, scraping, pinching, guided shooting, by tearing out hairs, or conducting the movement of a biopsy needle.

12. A device according to claim 1, further characterized in that one of the parts of the test capsule, which remains in the tissue of the animal whose sample was removed, includes a barcode, the readable and/or writeable integrated circuit, a magnetic strip, a transponder, a transmitter, a numerical code, a letter code, or a comparable coding or information carrier system or a simple color or analogous labeling.

13. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the device contains one or more magazines, in which test capsule covers, sample containers and parts of labelings can be loaded each time individually or in strips.

14. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the device makes available a mechanism, which in a first step, presses together the sample-removing part of the test capsule upon placing the device on the tissue and after actuating the trigger mechanism, in such a way that a tissue sample is removed by a pinching motion;

or, in a first step, upon placement of the device on the tissue and after actuating the trigger mechanism, advances the sample-removing part of the test capsule on the tissue such that a tissue sample is removed by a scraping motion;

or, in a first step, upon applying the device on the tissue and after actuating the trigger mechanism, advances the sample-removing part of the test capsule while squeezing together the sample remover at the tissue in such a way that hairs are torn out;

and in another step of the same course of movement or an additional actuating of the trigger mechanism joins the sample remover with another part of the test capsule to form the test capsule.

15. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the device makes available a possibility of associating the entered or automatically read-in serial numbers of the test capsules and the entered or automatically read-in information on the animal, whose sample has been taken, and other information concerning the respective sample removal; and storing these data on a storage medium along with the information on the association of these data.

16. A device according to claim 15, further characterized in that the storage medium is a) installed rigidly in the device or b) can be separated from it.

17. A device according to claim 15, further characterized in that said device includes an electronic unit, by means of which all stored data and information on the association of these data can be transmitted in a wireless manner and data can also be received, if need be, in a wireless manner.

18. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device characterized by the fact that the device is loaded with a sample container, formed out of one or two components, and a cover for sample containers, formed out of one or two components, whereby simultaneously the biological sample is taken and the sample container and the cover are joined to form the test capsule and together with taking the sample a labelling of the living being, from which the sample is taken, takes place by joining components of the sample container and the cover into the tissue of the living being, whereby the labelling of the living being, the labelling of the sample capsule are entered or read in and whereby these information are stored in order to achieve the correlation of the sample capsule and the living being.

19. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the device makes available a mechanism, which introduces a labeling on the animal, coupled with a removal of sample, which consists either of a) a simple color label or b) a self-adhering foil, c) an adhering badge or d) a self-adhering device or one that is rigidly anchored in the tissue, which carries one of a barcode, a readable and/or writeable integrated circuit, a magnetic strip, a transponder, a transmitter, a numerical code, a letter code, or a comparable coding or information carrier system or a simple color labeling.

20. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that one or more identical components of such test capsules are linked with one another;

the strips or rings that are formed of parts of test capsules can be loaded into the magazine or into an analogous device as units of more than only one such part of a test capsule;

the direction in which these strips or rings of several such units are loaded into the device is established by a labeling introduced on only one site of such a strip or ring;

the serial numbers of all such linked parts of test capsules are defined by only this one serial number in a clear manner.

21. A device according to claim 20, further characterized in that the serial number, which is introduced onto these strips or rings has a form that is automatically readable by a device provided for this purpose or must be read by the user himself and manually entered into a device provided for this purpose.

22. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the sample capsule has a site, which permits piercing with needles, pins, cannula or comparable devices.

23. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that said device comprises one or more parts, which can be separated, in order to remain as a labeling in the tissue of the living being, whose sample was removed.

24. A sample container for withdrawing biological samples, characterized by the fact that by means of a sample-removing device a tissue sample is removed from a living being, wherein by taking the sample a coded labeling of the living being and part of the sample-removing device takes place, said sample container further characterized in that after said sample container has been sealed by the test capsule cover, said sample container can be opened again or its contents can be reached only by leaving behind changes that can be discerned.

25. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the capsule also includes means for making an ear mark on an animal whose sample was removed after the test capsule has been joined.

26. A device according to claim 25, further characterized in that the ear mark remaining in the tissue can be removed only by leaving behind visible damage to either the ear mark or the animal.

27. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the sample-removing part of the test capsule on the side turned away from the sample has depressions, which serve for the purpose of pressing and squeezing the sample remover a) at the tissue in such a way that a tissue sample is removed by pinching or b) advancing it obliquely and under pressure at the tissue in such a way that a tissue sample is removed by scraping.

28. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components whereby the sample container and the cover are joined to form the test capsule, said device further characterized in that the sample container cover is slotted and partly conical, so that two or more tips will be easily punched into it upon contacting the test subject, and then are pressed together due to the conical shape, so that a small quantity of sample is sheared off or cut and no additional material will be removed.

29. A method for withdrawing biological samples, characterized by the fact that by means of a sample-removing device a tissue sample is removed from a living being, wherein by taking the sample a coded labeling of the living being and part of the sample-removing device takes place, said method further characterized in that the user of the device conducting the method must enter or confirm data before each or before a series of sample removals, in order to release the device.

30. A method for withdrawing biological samples, characterized by the fact that by means of a sample-removing device a tissue sample is removed from a living being, wherein by taking the sample a coded labeling of the living being and part of the sample-removing device takes place, said method further characterized in that all operating steps necessary for sample removal and labelling are coupled together in such a way that none of the operating steps can be conducted individually.

31. A method for withdrawing biological samples, characterized by the fact that by means of a sample-removing device a tissue sample is removed from a living being, wherein by taking the sample a coded labeling of the living being and part of the sample-removing device takes place, said method further characterized in that a labeling of the living being from which a sample is removed is conducted during or coupled with the actual sample removal.

32. A method for withdrawing biological samples, characterized by the fact that by means of a sample-removing device a tissue sample is removed from a living being, wherein by taking the sample a coded labeling of the living being and part of the sample-removing device takes place, said method further characterized in that the labeling cannot be removed after said labeling has been introduced on the living being or said labeling can be removed only by disrupting or damaging said labeling or damaging the living being.

33. A method for withdrawing biological samples, characterized by the fact that by means of a sample-removing device a tissue sample is removed from a living being, wherein by taking the sample a coded labeling of the living being and part of the sample-removing device takes place, said method further characterized in that the labeling includes:
  a barcode,
  a readable and/or writeable integrated circuit,
  a magnetic strip,
  a transponder,
  a transmitter,
  a numerical code,
  a letter code or
  a comparable coding or information carrier system
  or a simple color labeling.

34. A method according to claim 33, further characterized in that a test capsule is sealed in a way, which makes it impossible to open the test capsule again without obvious changes to this test capsule.

35. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that a test capsule is sealed in a way, which makes it impossible to open the test capsule again without obvious changes to said test capsule.

36. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that after it has been sealed by the test capsule cover, it can be opened again or its contents can be reached only by leaving behind changes that can be discerned.

37. A test capsule for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said test capsule further characterized in that individual sample containers or several sample containers joined together in a chain make available one serial number, which is introduced during manufacture or later.

38. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that parts of the test capsule are filled with reagents necessary for the further processing of the sample.

39. A device for withdrawing biological samples, characterized by the fact that by means of a sample-removing device a tissue sample is removed from a living being, wherein by taking the sample a coded labeling of the living being and part of the sample-removing device takes place, said device consisting of a sample container, formed out of one or two components, and a cover for sample containers, formed out of one or two components, whereby the sample container and the cover are joined to form the test capsule, said device further characterized in that the device

- can read the labeling of the sample containers either automatically or this information can be received and processed by the user,
- data on the identity of the sample to be removed are automatically or manually recorded,
- the data on the consecutive numbering of the sample vessels are automatically associated with the data on the sample by the removal device,
- data on the sample vessel number and sample are stored on a common storage medium,
- the stored data are transmitted to the analytical device by means of direct data transmission from the removal device or from an additional device or by transport of a data carrier that can be separated.

* * * * *